(12) United States Patent
Andreucci et al.

(10) Patent No.: US 10,175,212 B2
(45) Date of Patent: Jan. 8, 2019

(54) SYSTEM AND METHOD FOR ANALYZING A GAS

(71) Applicants: California Institute of Technology, Pasadena, CA (US); Commissariat à l'Energie Atomique et aux Energies Alternatives, Paris (FR); Apix Analytics, Grenoble (FR)

(72) Inventors: Philippe Andreucci, Moirans (FR); Eric Colinet, Grenoble (FR); Laurent Duraffourg, Voiron (FR); Edward Myers, Sherman Oaks, CA (US); Mélanie Petitjean, Baudonvilliers (FR); Mickael Lee Roukes, Pasadena, CA (US); Joshua Whiting, Springboro, OH (US)

(*) Notice: Subject to any disclaimer, the term of this patent is extended or adjusted under 35 U.S.C. 154(b) by 469 days.

(21) Appl. No.: 14/558,219

(22) Filed: Dec. 2, 2014

(65) Prior Publication Data
US 2015/0308990 A1  Oct. 29, 2015

(30) Foreign Application Priority Data

Dec. 2, 2013 (WO) .................. PCT/IB2013/003247

(51) Int. Cl.
*G01N 30/64* (2006.01)
*G01N 29/02* (2006.01)
(Continued)

(52) U.S. Cl.
CPC ............. *G01N 30/64* (2013.01); *G01N 9/002* (2013.01); *G01N 11/00* (2013.01); *G01N 11/04* (2013.01);
(Continued)

(58) Field of Classification Search
CPC ......... G01N 30/64; G01N 30/78; G01N 11/04
(Continued)

(56) References Cited

U.S. PATENT DOCUMENTS 6,311,549 B1 * 11/2001 Thundat ................. G01N 9/002
73/24.05
6,722,200 B2 * 4/2004 Roukes .................... G01G 3/16
73/32 A
(Continued)

FOREIGN PATENT DOCUMENTS

EP    1746414 A2    1/2007
EP    2008965 A2    12/2008
(Continued)

OTHER PUBLICATIONS

Fanget, S. et al., Gas sensors based on gravimetric detection—A review, Elsevier, Sensors and Actuators B 160 804-821. (2011).
(Continued)

*Primary Examiner* — David M Gray
*Assistant Examiner* — Andrew V Do
(74) *Attorney, Agent, or Firm* — Lerner, David, Littenberg, Krumholz & Mentlik, LLP

(57) ABSTRACT

A gas analysis system includes a fluidic channel for flow of a gas to be analyzed, a detector in the channel and adapted for measuring interactions of the gas with the detector, the detector including a resonator of the electromechanical nanosystem (NEMS) type and a heating system for heating a part of the detector, an actuation device for vibrationally actuating the resonator according to an excitation signal applied to an input of the detector, a detection device adapted for providing an output electric signal representative of the vibrations of the resonator, a read-out device connected to an input of the detector and configured for simultaneously measuring, from the output signal of the detector, the change in resonance frequency and the change in amplitude of the vibrations at the resonance frequency of the resonator, and a processing device configured for determining from the changes a fluidic characteristic of the gas.

24 Claims, 16 Drawing Sheets

Figure 1:
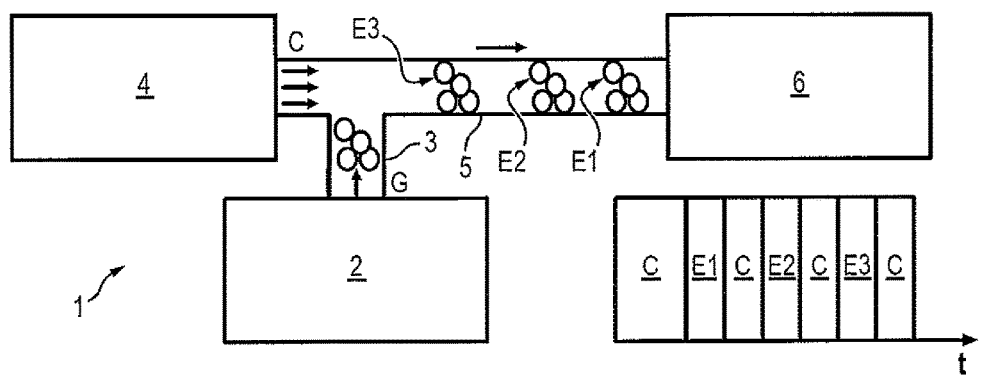

(51) Int. Cl.
*G01N 9/00* (2006.01)
*G01N 11/00* (2006.01)
*G01N 30/78* (2006.01)
*G01N 29/032* (2006.01)
*G01N 29/036* (2006.01)
*G01N 29/22* (2006.01)
*G01N 11/04* (2006.01)
*B82Y 15/00* (2011.01)

(52) U.S. Cl.
CPC ......... *G01N 29/022* (2013.01); *G01N 29/032* (2013.01); *G01N 29/036* (2013.01); *G01N 29/222* (2013.01); *G01N 30/78* (2013.01); *B82Y 15/00* (2013.01); *G01N 2009/006* (2013.01); *G01N 2291/021* (2013.01); *G01N 2291/02818* (2013.01); *G01N 2291/106* (2013.01)

(58) Field of Classification Search
USPC .............................................. 73/24.01, 24.06
See application file for complete search history.

(56) References Cited

U.S. PATENT DOCUMENTS

| | | | | |
|---|---|---|---|---|
| 6,732,567 | B2 * | 5/2004 | Briscoe | F04B 19/006 73/23.2 |
| 8,291,745 | B2 * | 10/2012 | Karabacak | G01N 29/022 73/24.01 |
| 2013/0074586 | A1 | 3/2013 | Blanco-Gomez et al. | |
| 2014/0076024 | A1 * | 3/2014 | Duraffourg | G01N 25/18 73/23.4 |

FOREIGN PATENT DOCUMENTS

| | | |
|---|---|---|
| EP | 2141490 A1 | 1/2010 |
| WO | 0122056 A1 | 3/2001 |
| WO | 2006119167 A1 | 11/2006 |
| WO | 2011154362 A1 | 12/2011 |
| WO | 2012034951 A1 | 3/2012 |
| WO | 2012034990 A1 | 3/2012 |
| WO | 2012172204 A1 | 12/2012 |

OTHER PUBLICATIONS

Mile, F, et al., In-plane nanoelectromechanical resonators based on silicon nanowire piezoresistive detection, Condensed Matter Physics 114-35, California Institute of Technology, 2010.

Yongha Hwang et al: "Porous Silicon Resonators for Improved Vapor Detection", Journal of Microelectromechanical Systems, IEEE Service Center, US, vol. 21. No. 1, Feb. 1, 2012 (Feb. 1, 2012), pp. 235-242. XP011403353, ISSN: 1057-7157, DOI: 10.1109/JMEMS.2011.2170819 the whole document.

Xu, Yang, et al., Viscous damping of microresonators for gas composition analysis, Applied Physics Letters 88, 143513 (2006).

Arcamone, J., et al., VLSI silicon multi-gas analyzer coupling gas chromatography and NEMS detectors, Condensed Matter Physics MC 149-33, California Institute of Technology, 2011.

Bao, M., et al., Squeeze film air damping in MEMS, Elsevier, Sensors and Actuators A 136 (2007) 3-27.

Bargatin, I. et al., Large-Scale Integration of Nanoelectromechanical Systems for Gas Sensing Applications, Kavli Nanoscience Institute and Department of Physics, Caltech, American Chemical Society 2012.

International Search Report for Application No. PCT/IB2013/003247 dated Aug. 12, 2014.

* cited by examiner

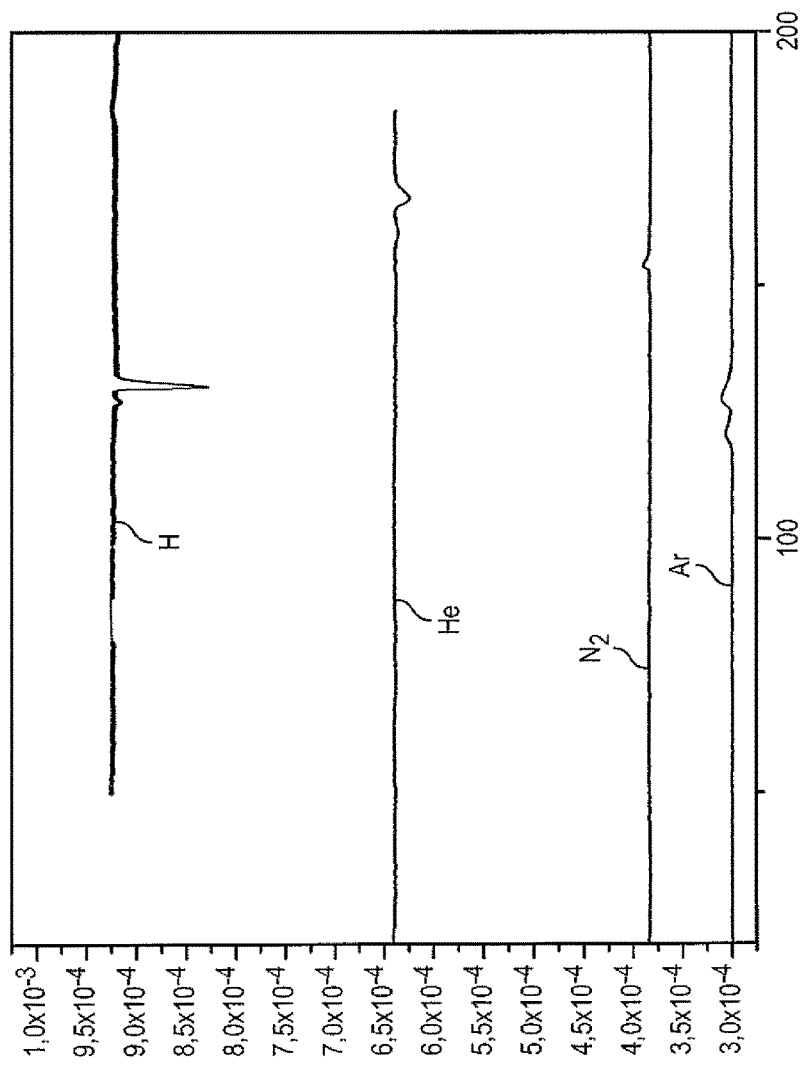

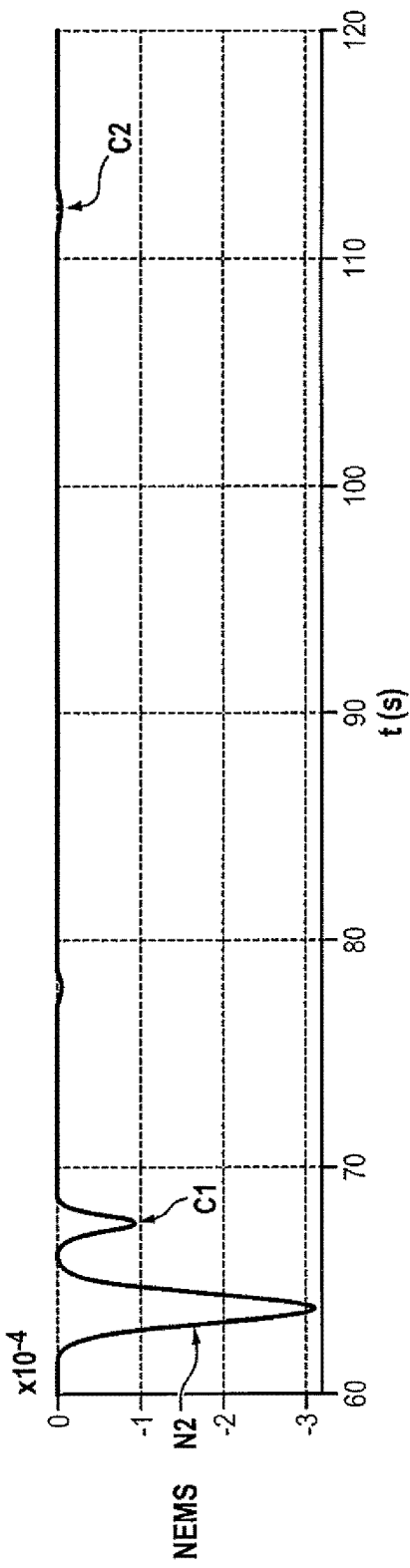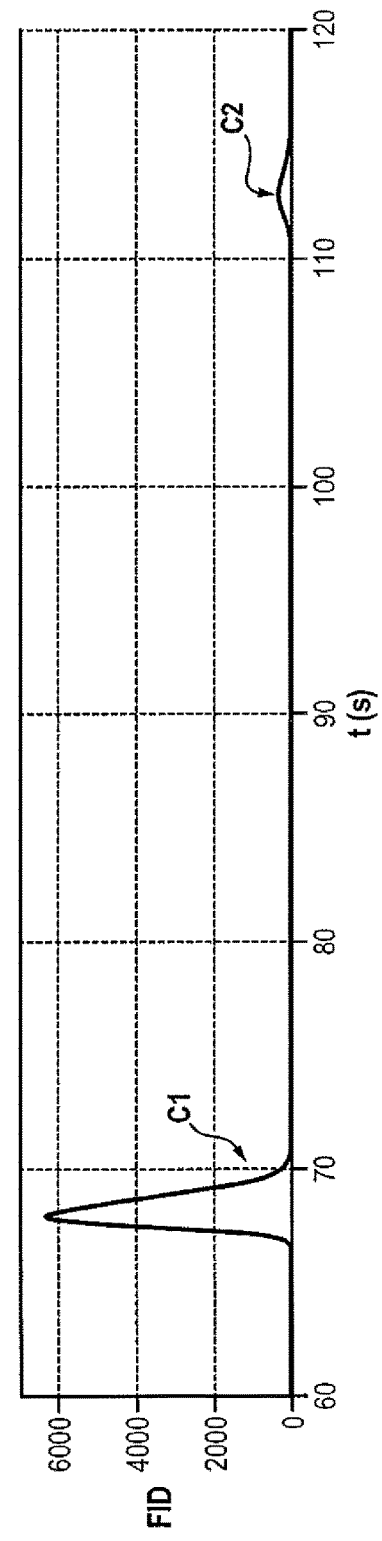

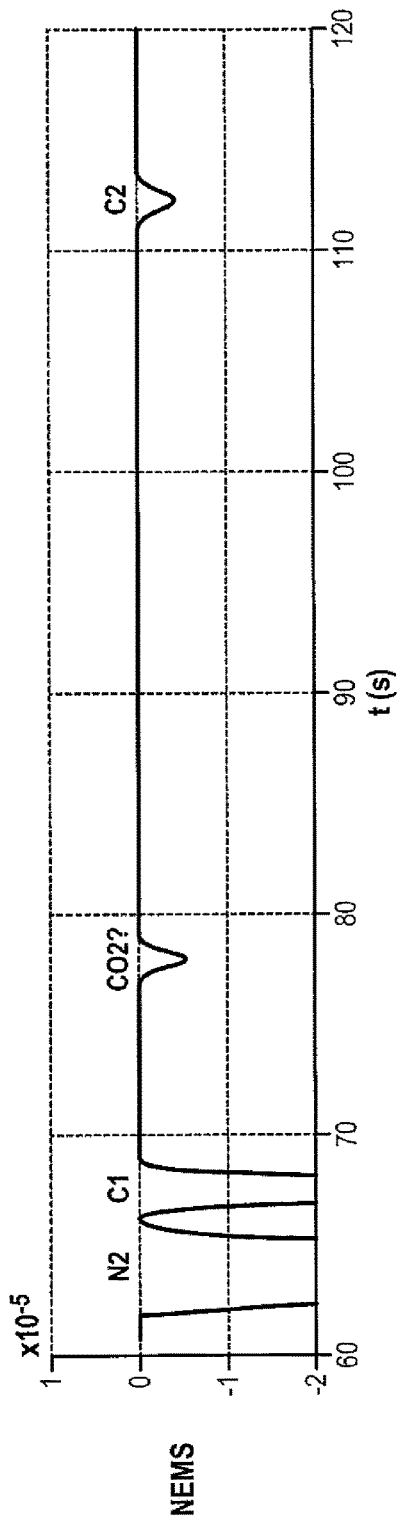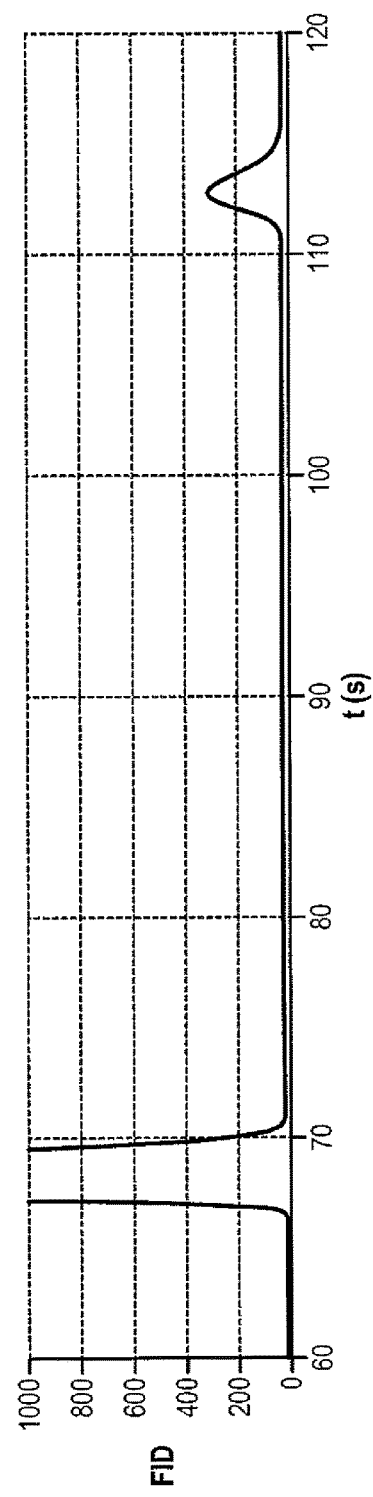

SYSTEM AND METHOD FOR ANALYZING A GAS

CROSS REFERENCE TO RELATED APPLICATIONS

The present application claims priority from PCT/IB2013/003247, filed Dec. 2, 2013, the disclosure of which is hereby incorporated herein by reference.

FIELD OF THE INVENTION

The present invention relates to a gas analysis system comprising a fluidic channel intended for the flow of a gas to be analyzed and at least one detector of the electromechanical nanosystem type laid out in same fluidic channel.

BACKGROUND OF THE INVENTION

Measurement of the properties of a gas with a view to determining the composition generally resorts to associating a chromatography column, which allows separation in time of different species contained in the gas to be analyzed according to their affinity with a stationary phase laid out in the column, and one or several detectors placed at the outlet of said column, each detector being adapted so as to measure a particular property of the species of the gas to be analyzed.

At the present time, the detectors used are intended for measuring physical properties of the gas.

Among the detectors frequently used, mention may be made of Flame Ionization Detectors (FID) which allow measurement of the combustion energy of a gas; Thermal Conductivity Detectors (TCD) which allow measurement of the heat conductivity of a gas; chemical detectors known under the name of «chemiresistors» which allow evaluation of the chemical affinity of the gas towards a chemical species.

Gravimetric detectors, including resonators of the MEMS (electromechanical microsystem) or NEMS (electromechanical nanosystem) type also allow evaluation of the chemical affinity of the gas towards a functionalized layer deposited at the surface of the resonator [Fanget 2011].

Indeed, the adsorption of the species contained in the gas on the functionalized layer causes change in the mass and therefore in the resonance frequency of the resonator, this change in the resonance frequency allowing determination of a physical property of the gas.

NEMS detectors are particularly promising as detectors coupled with a chromatography column [Arcamome 2011].

However, depending on the gas to be analyzed, the gravimetric measurement carried out by means of these resonators has certain limitations.

On the one hand, NEMS detectors do not allow detection of volatile species since these species are not adsorbed on the functionalized layer of the resonators.

Moreover, NEMS detectors do not allow detection by gravimetry of rare or inert gases (such as $N_2$, $O_2$, Ar, He, etc.), since there is no possible chemical interaction with a functionalized layer deposited on the resonator.

On the other hand, for highly concentrated gases, saturation of the functionalized layer by the concentrated species may occur especially when the functionalization layers are thin (from a few nanometers to a few tens of namometers), which does not allow a reliable measurement.

The saturated concentrations in the chemical functionalization layers depend on the type of layer, on the layer thickness and especially on the type of gas involved. They may for example be of several tens of %.

In other words, these NEMS detectors are mainly adapted for detecting heavy species and/or moderately concentrated species.

A use of MEMS or NEMS detectors for measuring fluidic interactions between the resonator and a gas which are expressed by damping of the vibrations of the resonator according to the molar mass of the gas has been described in [Xu 2006].

Thus, the measurement of the change in the resonance frequency of the resonator allows determination of the molar mass of the gas, even in the absence of chemical interaction between the resonator and the gas.

However, such a measurement can only be carried out for sufficiently concentrated gases.

Now, in the design of a gas analysis system, it is generally sought to make this system «universal», i.e. capable of analyzing any gas, notably complex mixtures.

SHORT DESCRIPTION OF THE INVENTION

An object of the invention is therefore to improve the detection capabilities of NEMS detectors and to make them in particular capable of detecting volatile species and/or highly concentrated species in a gas.

Another object of the invention is to design a gas analysis system comprising one or several NEMS detectors and capable of analyzing any gas accurately.

The invention thus provides a gas analysis system comprising:
- a fluidic channel intended for the flow of a gas to be analyzed,
- at least one detector laid out in said fluidic channel and adapted for measuring interactions of the gas with said detector, said detector comprising at least one resonator of the electromechanical nanosystem (NEMS) type and a heating system for heating at least a part of the detector,
- an actuation device for vibrationally actuating the resonator according to an excitation signal applied to an input of the detector, and
- a detection device adapted for providing an output electric signal representative of the vibrations of said resonator,
- a read-out device connected to an input of the detector and configured for simultaneously measuring, from the output signal of said at least one detector, the change in resonance frequency and the change in amplitude of the vibrations at the resonance frequency of the resonator, and
- a processing device configured for determining from said changes at least one fluidic characteristic of said gas.

By resonator, is meant in the present text a member capable of resonating under the application of an excitation signal.

Generally, the resonator appears as a suspended beam relatively to a support.

Moreover, in any NEMS detectors, said resonator is of nanometric size, i.e. at least one of its dimensions is less than 1 micrometer.

According to a preferred embodiment, the fluidic characteristic of said gas is a viscosity and/or an effective viscosity and/or a chemical affinity and/or a mean free path of molecules of the gas and/or a flow rate of said gas and/or the heat conductivity of said gas.

By effective viscosity is meant a viscosity coefficient taking into account the effect of gas rarefaction in the Reynolds equation simplifying the Navier-Stokes equation. In this respect, reference may be made to paragraph 5.1 of [Bao 2007].

As this will be discussed in detail below, the design of said analysis system is based on the capability of nanometric resonators of having with a surrounding gas non-negligible interactions (so-called fluidic interactions) at the relevant scales, which make it possible to measure at least one fluidic property of the gas to be analyzed, said property being preferentially viscosity and/or effective viscosity of the fluid, but also if necessary the chemical affinity of the gas with the resonator, which is functionalized in this case with a dedicated chemical deposited on its surface, the mean free path of gas molecules and/or the fluid flow rate.

According to an embodiment, the system comprises a plurality of detectors electrically connected in parallel so as to form at least one network having:
  at least one input for applying, with the read-out device,
    at least one excitation signal in vibration, to the whole of the detectors of the network, and
  at least one output for providing a signal resulting from the output signals of each of the detectors of the network.

Said resulting signal may include the different output signals of the detectors provided in series and the processing device may thus be configured for calculating an average of the output signal of the detectors of the network.

According to an embodiment, the fluidic channel locally has a restriction and/or a widening of its cross-section and the system comprises detectors or networks of detectors laid out in portions of the fluidic channel having different cross-sections.

According to an embodiment, the system further comprises a chromatography column, the fluidic channel being laid out in at least a downstream portion of the chromatography column relatively to the direction of flow of the gas and at least a portion of said detectors or network of detectors being in said column.

According to an embodiment, the system comprises at least two detectors or networks of detectors, the resonators of which are functionalized with different chemical species.

According to an embodiment, at least two detectors of a same network of two detectors of networks of distinct detectors have at least one different geometrical characteristic.

Said at least one different geometrical characteristic of a detector may be selected from: the thickness of at least one resonator, the length of at least one resonator, the width of at least one resonator, the distance between at least one resonator and the actuation device.

According to an embodiment, the system comprises a vacuum pump downstream from said fluidic channel.

According to an embodiment, the processing device is further configured for applying an algorithm with which the frequency and amplitude variation measurements may be merged.

According to an embodiment, the read-out device comprises a phase locked loop (PLL).

Alternatively, the read-out device may comprise an oscillator.

According to an embodiment, the read-out device is configured, for a selected resonance mode of the detector, for measuring the resonance frequency on said selected resonance mode of the detector and optionally for measuring the amplitude of the vibrations on at least one higher resonance mode than said selected mode.

According to an embodiment, the resonator is a beam clamped at one of its ends and free at the opposite end and the detection device comprises two piezo-resistive strain gauges laid out on either side of said beam in the vicinity of the clamped end, the heating system being configured to heat the strain gauges by Joule effect.

Alternatively, the resonator is a beam clamped at both ends and the heating system is configured to heat the beam by Joule effect.

According to an embodiment, the system comprises at least one detector or network of detectors, each resonator of which is functionalized with a porous layer.

Another aspect of the invention provides a method for analyzing a gas, wherein:
  a gas to be analyzed is injected into a system as described above,
  at least one resonator of a detector or network of detectors of said system is actuated for causing vibration of said resonator at a resonance frequency,
  an output signal representative of the vibration of the resonator or of the whole of the resonators of said detector or network of detectors is read out, and
  the resonance frequency and the amplitude of the vibrations at the resonance frequency of each detector are measured from the output signal simultaneously.

According to an embodiment, a depression is applied in the fluidic channel in which is laid out said at least one detector or network of detectors.

According to an embodiment, the gas to be analyzed is injected into the system with a carrier gas and said carrier gas is selected so that it has at least one fluidic characteristic different from that of the gas to be analyzed.

Said at least one fluidic characteristic may be a viscosity and/or an effective viscosity and/or a chemical affinity with the resonator and/or a mean free path of molecules of the gas and/or a flow rate of said gas and/or a heat conductivity of said gas.

According to an embodiment, the gas is heated upstream from the detector or from the network of detectors and/or said detector or network of detectors is heated so as to increase the contrast between said different fluidic characteristic of the carrier gas and that of the gas to be analyzed.

According to an embodiment, a merging algorithm is applied with which the frequency and amplitude variation measurements may be merged.

Another object of the invention provides a method for analyzing a gas, wherein:
  a gas to be analyzed is injected into a gas analysis system comprising:
    a fluidic channel intended for the flow of a gas to be analyzed,
    at least one detector laid out in said fluidic channel and adapted for measuring interactions of the gas with said detector, said detector comprising at least one resonator of the electromechanical nanosystem (NEMS) type,
    an actuation device for vibrationally actuating the resonator according to an excitation signal applied to an input of the detector, and
    a detection device adapted for providing an output electric signal representative of the vibrations of said resonator,
    a read-out device connected to an input of the detector and configured for simultaneously measuring, from the output signal of said at least one detector, the change in resonance frequency and the change in amplitude of the vibrations at the resonance frequency of the resonator, and a processing device configured for determining from said changes at least one fluidic characteristic of said gas, at least one resonator of a detector or network of detectors of said system is actuated for causing vibration of said resonator at a resonance frequency, an output signal representative of the vibration of the resonator or of the whole of the resonators of said detector or network of detectors is read out, and the resonance frequency and the amplitude of the vibrations at the resonance frequency of each detector are measured from the output signal simultaneously, wherein the resonance frequency is measured on a selected resonance mode of the detector and the amplitude of the vibrations is measured on at least one higher resonance mode than said selected mode.

SHORT DESCRIPTION OF THE DRAWINGS

Figure 2:
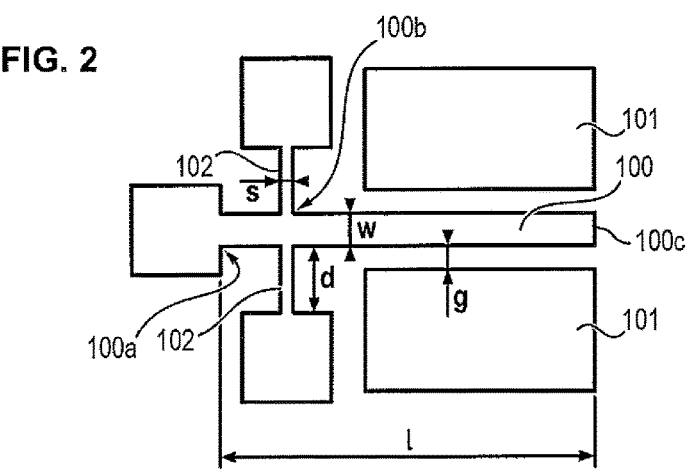
Figure 3:
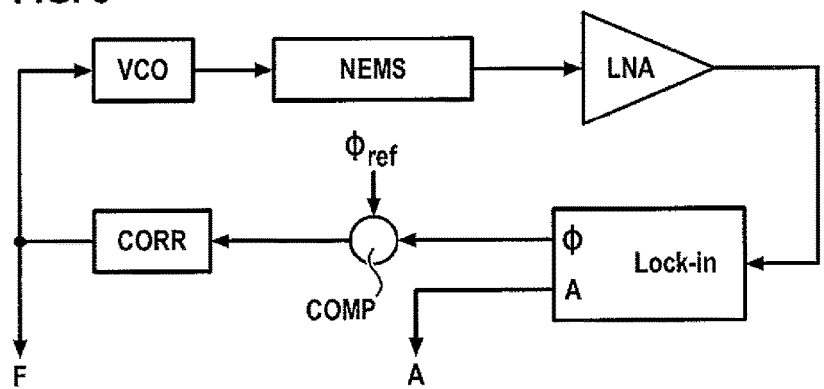
Figure 4:
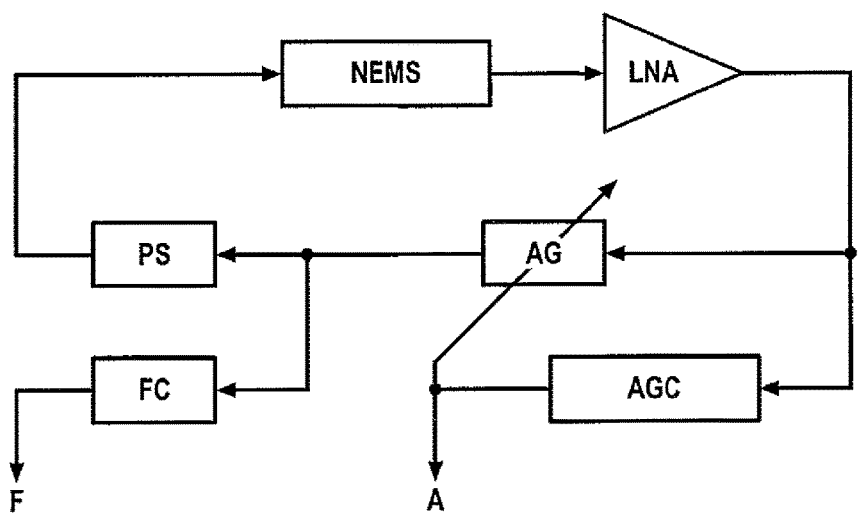
Figure 5:
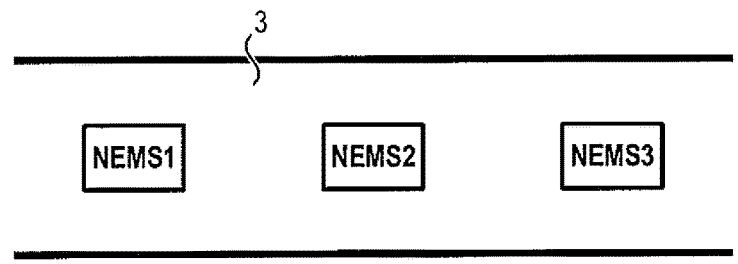
Figure 6:
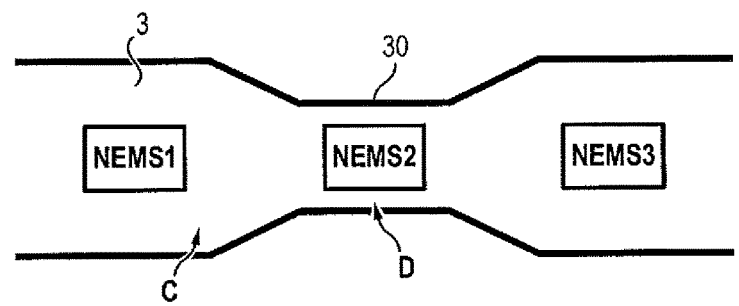
Figure 7:
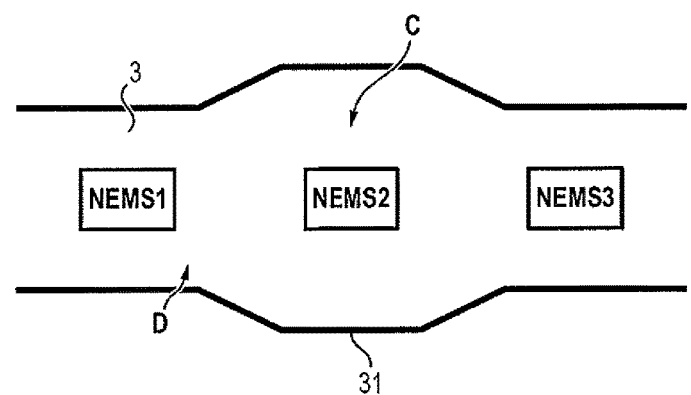
Figure 8:
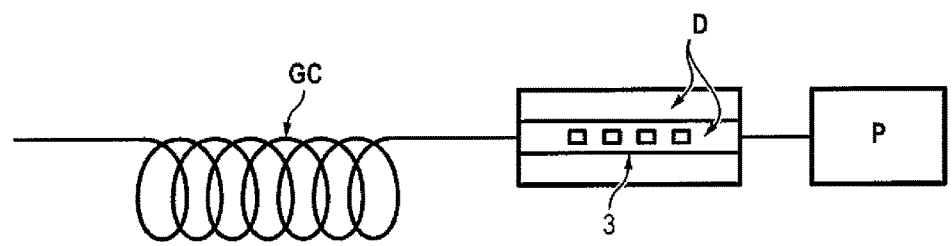
Figure 9A:
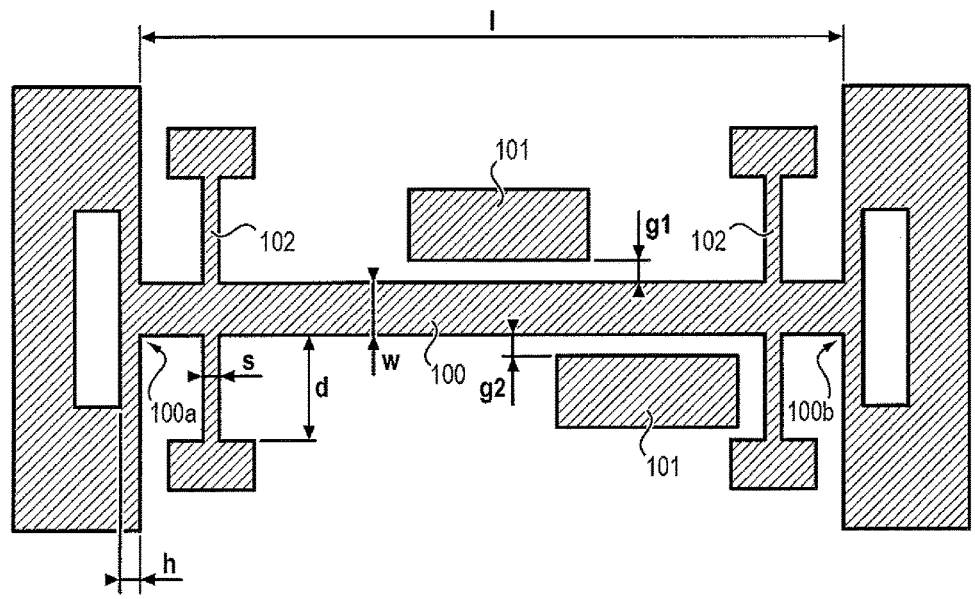
Figure 9B:
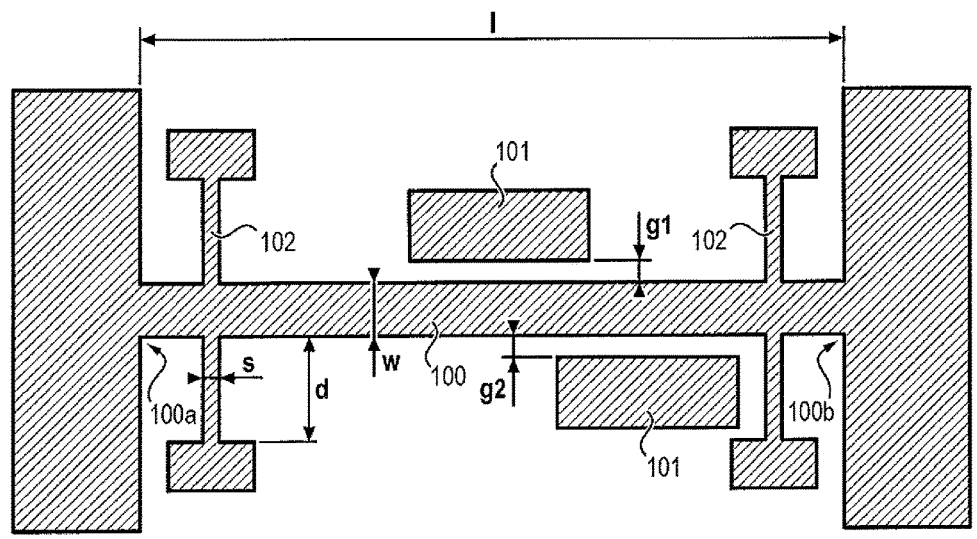
Figure 10:
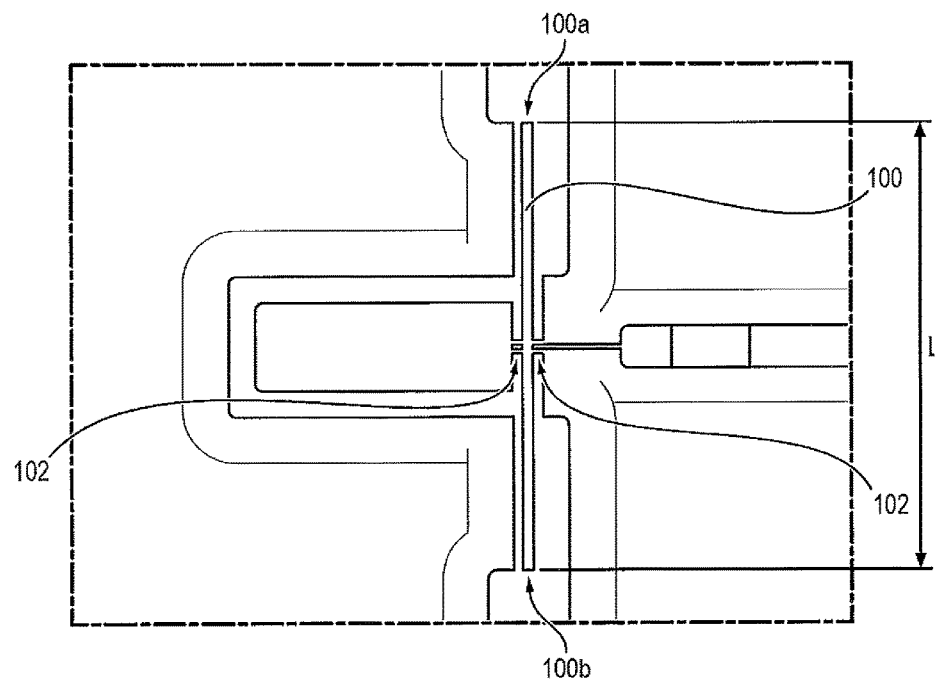
Figure 11:
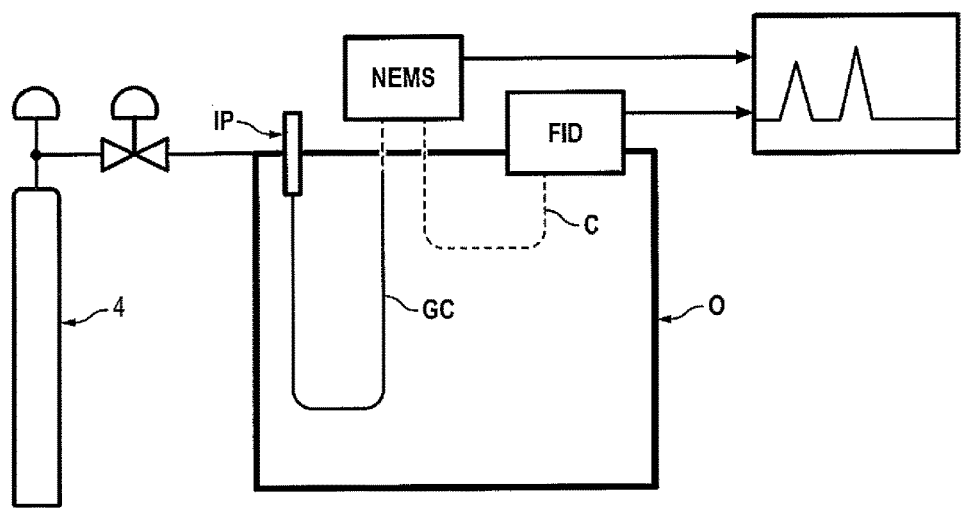
Figure 12A:
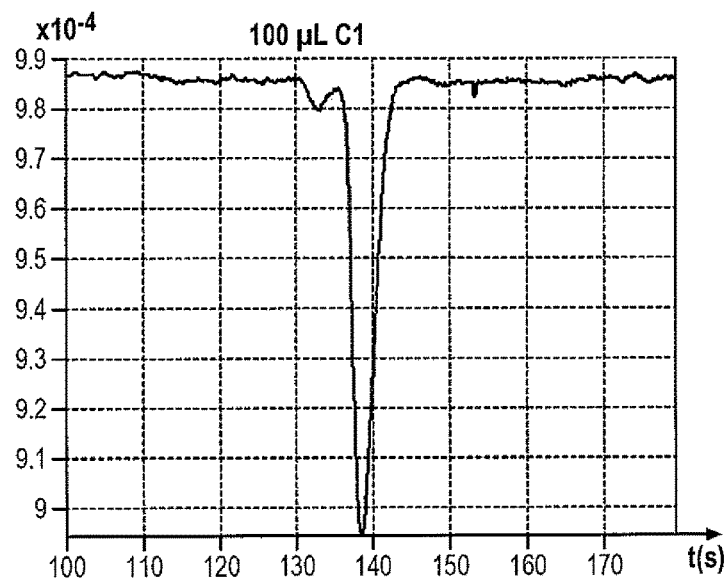
Figure 12B:
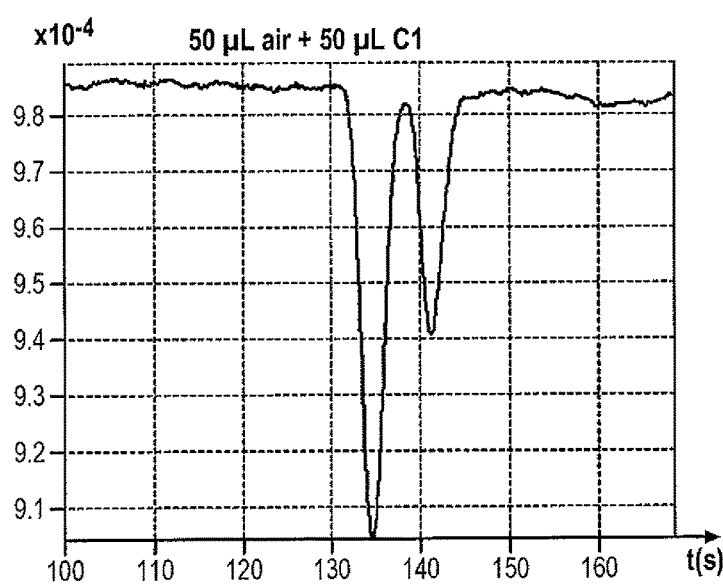
Figure 12C:
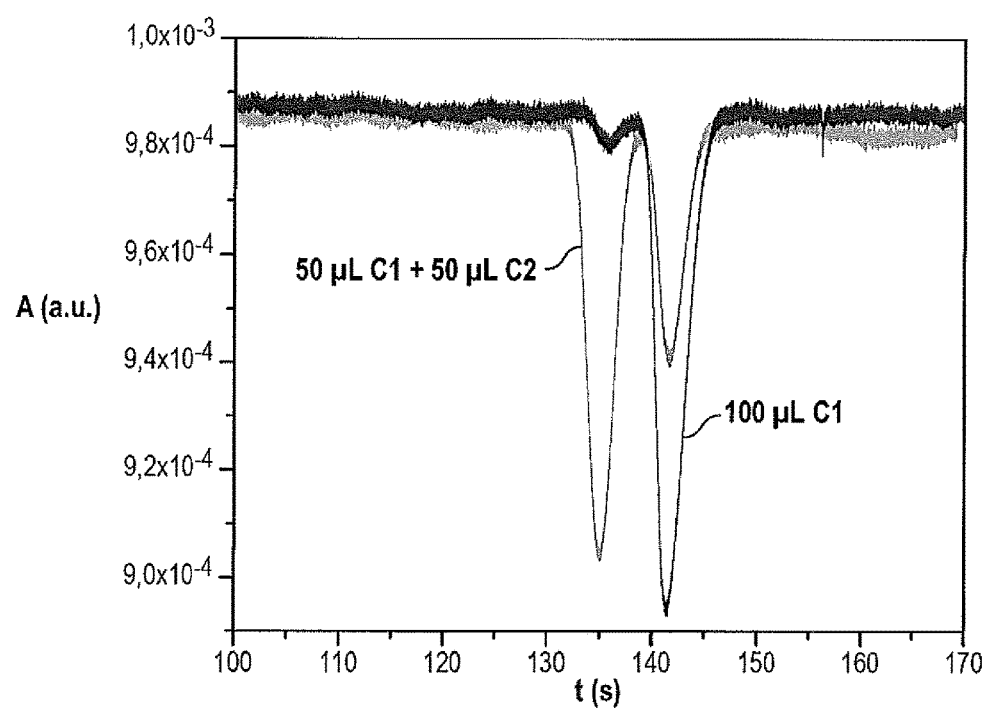
Figure 13:
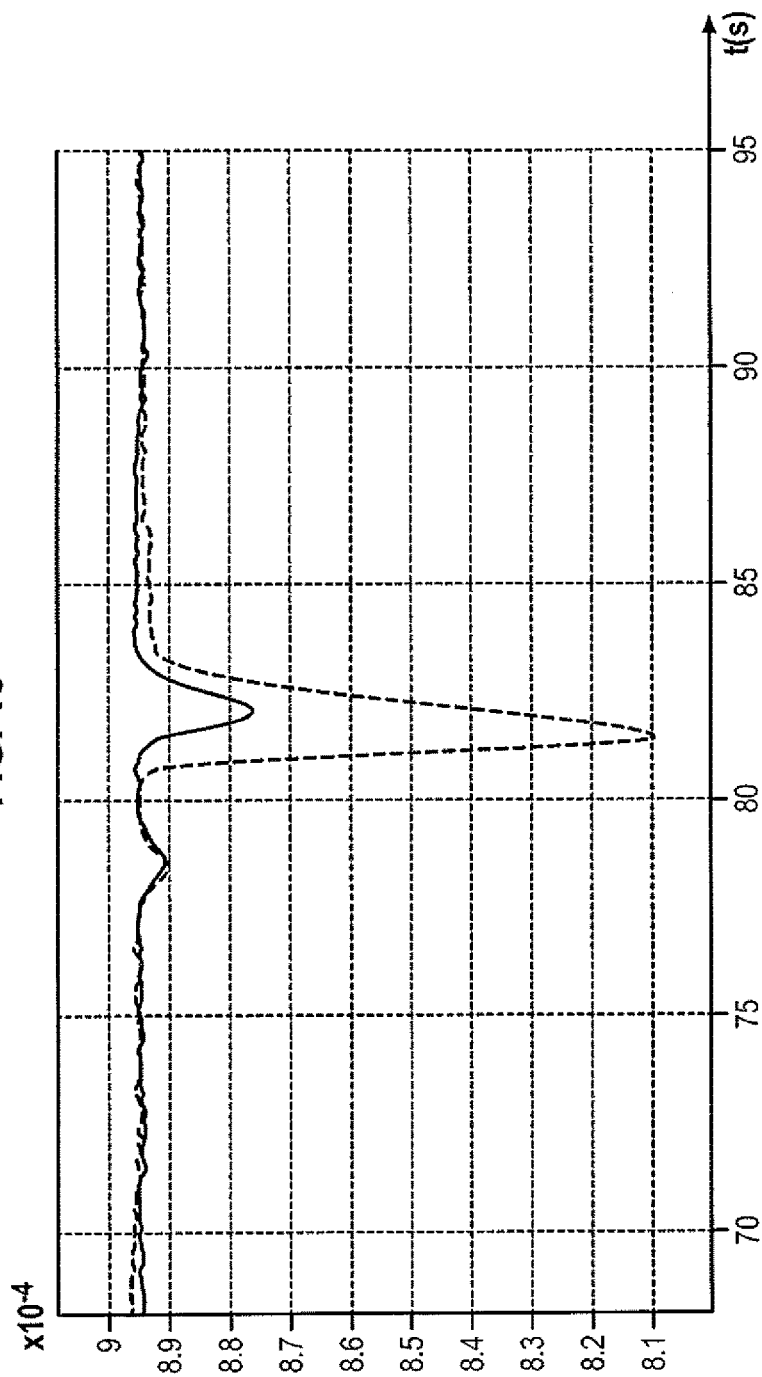
Figure 14A:
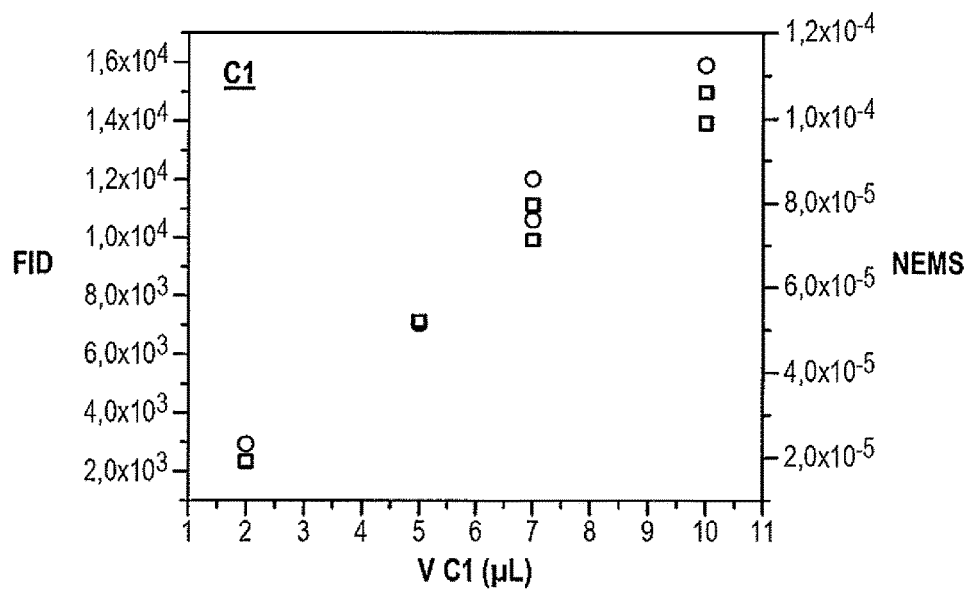
Figure 14B:
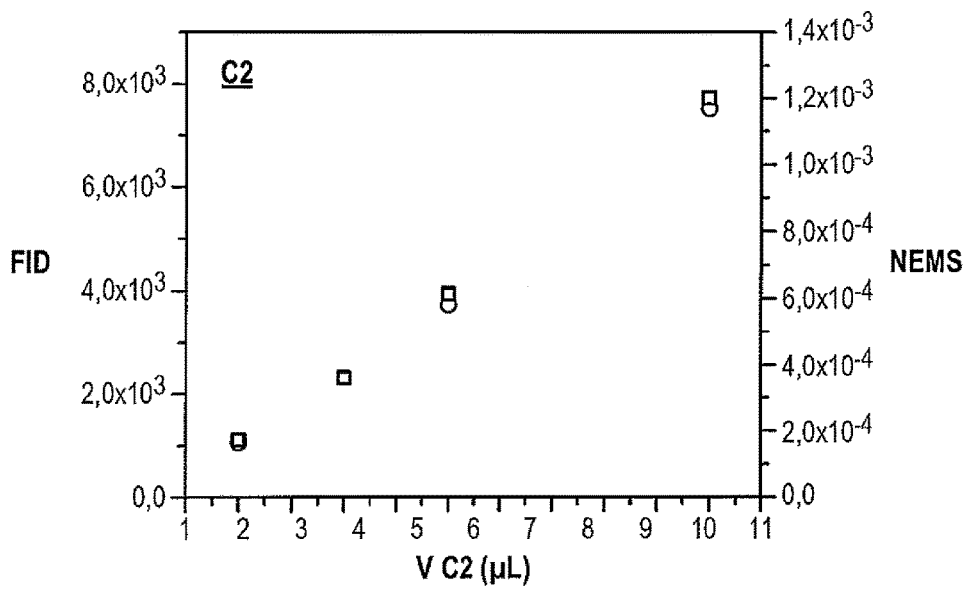
Figure 16A:
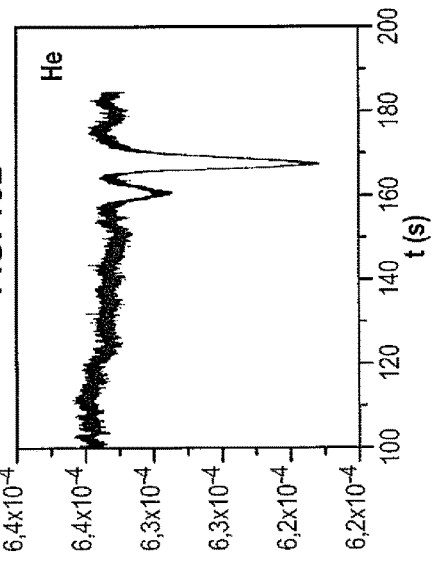
Figure 16B:
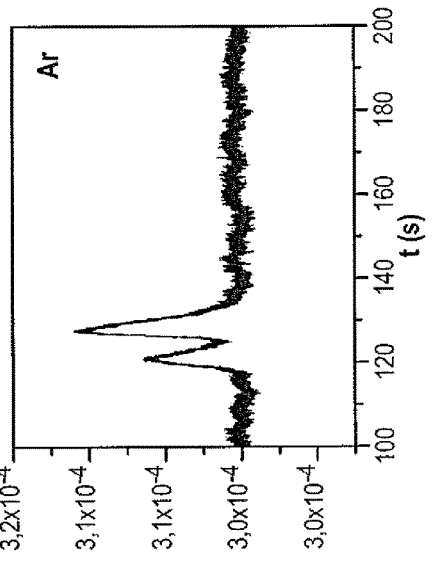
Figure 16C:
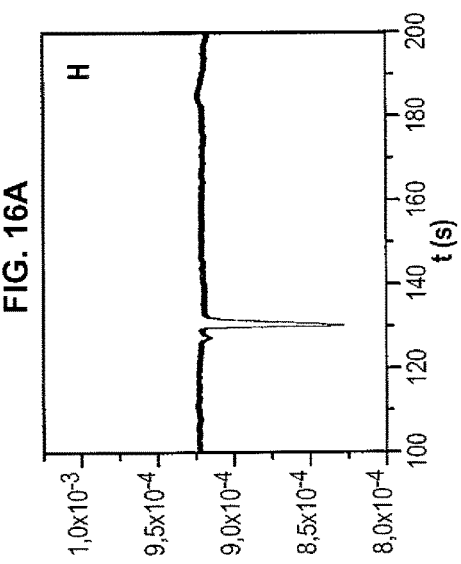
Figure 16D:
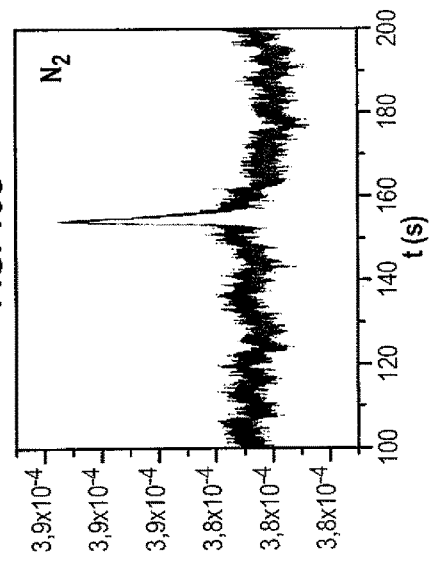
Figure 18:
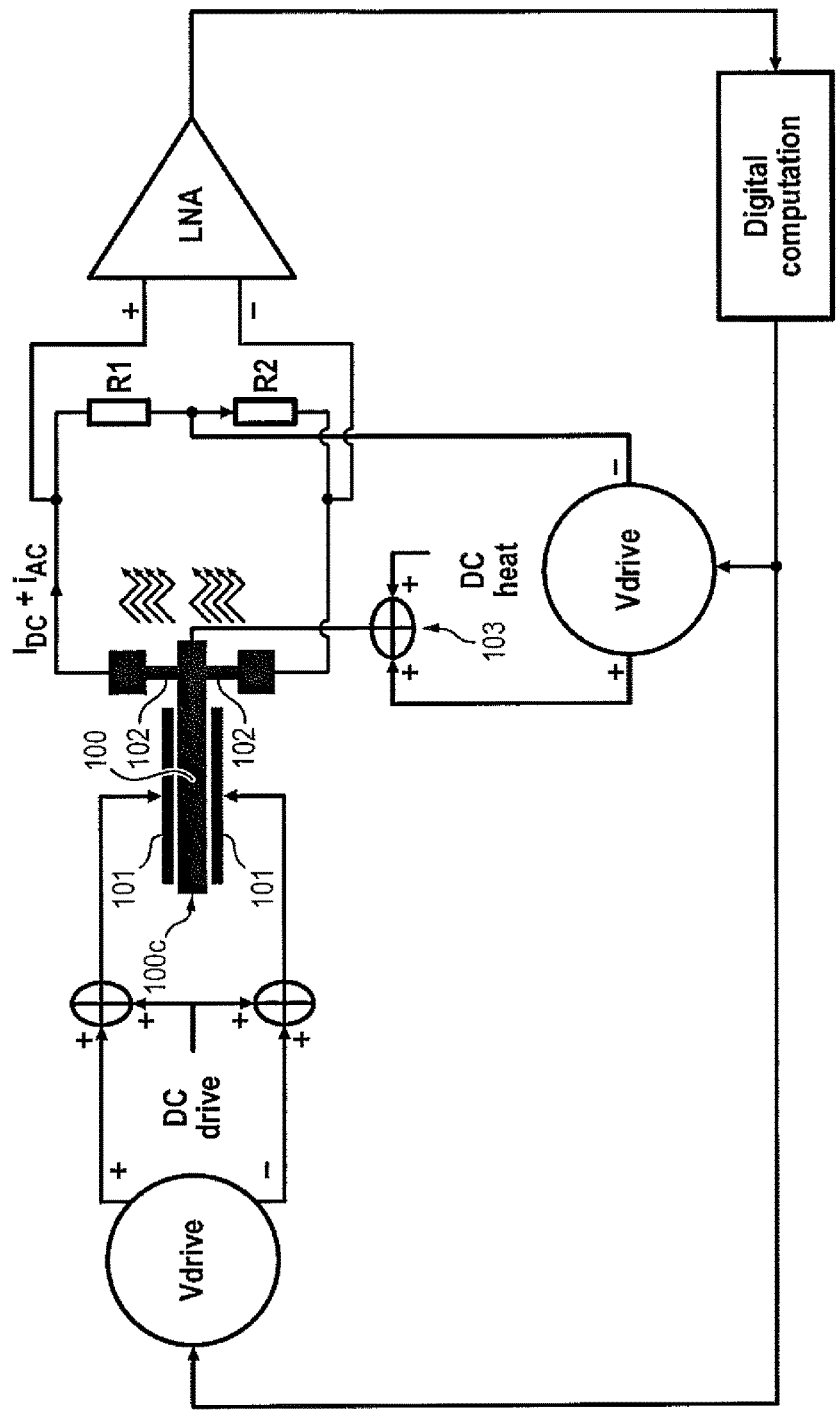
Figure 19:
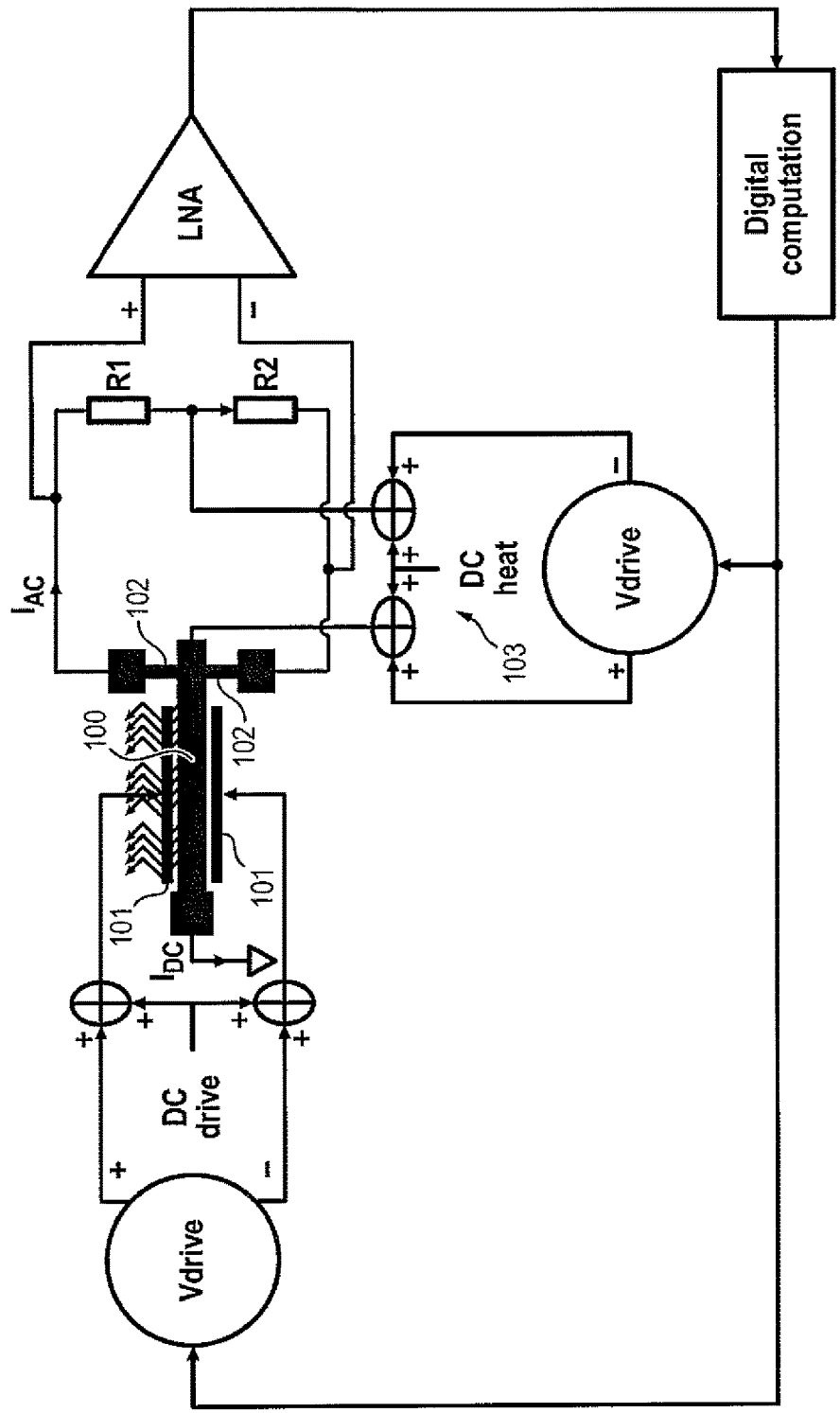
Figure 20:
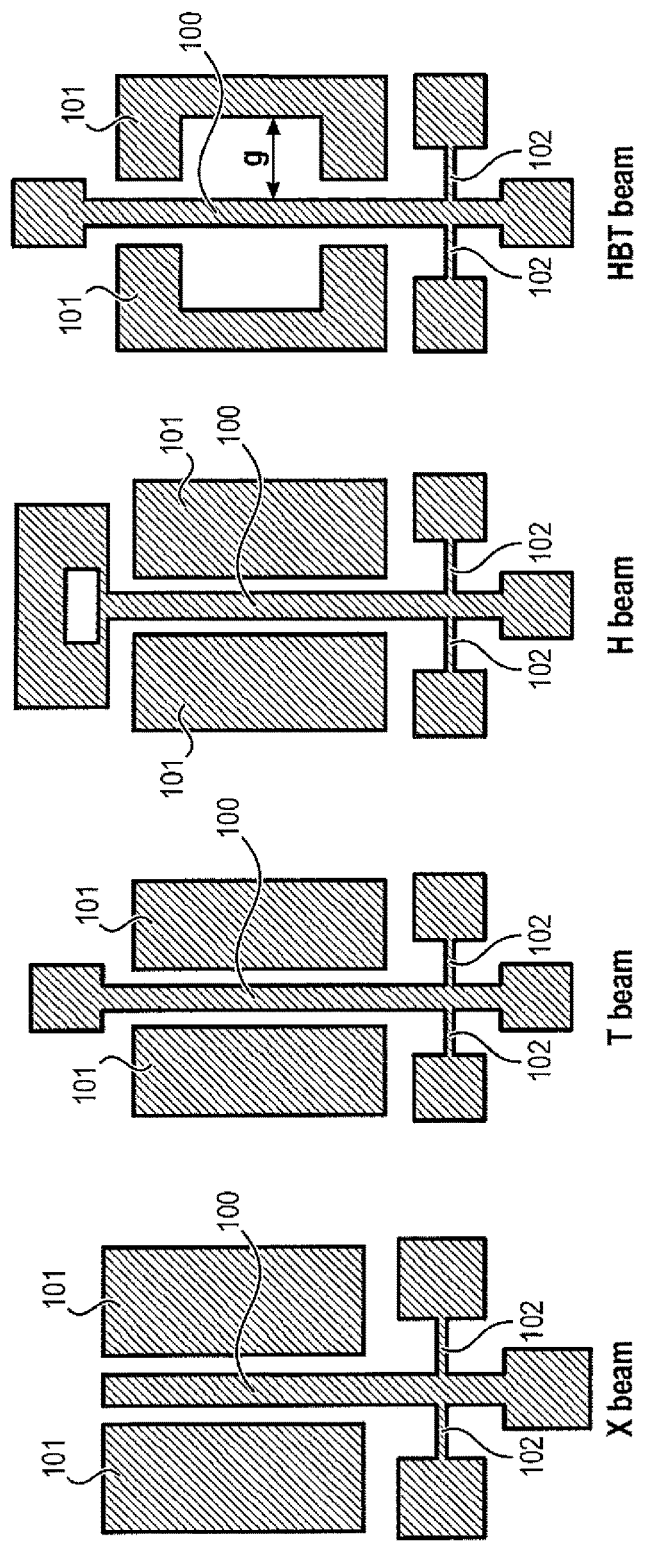

Other features and advantages of the invention will become apparent from the detailed description which follows, with reference to the appended drawings wherein:

FIG. 1 is a block diagram of a gas analysis system,

FIG. 2 is a diagram of an embodiment of a NEMS detector which may be applied in an analysis system according to the invention, FIG. 3 is a block diagram of the electronic read-out circuit according to an embodiment of the invention, FIG. 4 is a block diagram of the electronic read-out circuit according to another embodiment of the invention, FIGS. 5 to 7 illustrate various configurations of a fluidic channel in which are laid out several NEMS detectors, FIG. 8 is a block diagram of an embodiment of a system comprising a chromatography column and a vacuum pump, FIGS. 9A, 9B, and 10 are diagrams of advantageous embodiments of a detector which may be applied in an analysis system according to the invention, FIG. 11 is a block diagram of an experimental circuit for validating a gas analysis system according to an embodiment of the invention, FIGS. 12A to 12C show nitrogen and methane detection curves obtained experimentally, FIG. 13 shows nitrogen and methane detection curves obtained for different injected amounts of methane, FIGS. 14A and 14B show the respective responses of a reference FID detector and of an NEMS detector for different injected amounts of methane and ethane, FIG. 15 shows the methane detection curves for various carrier gases, FIGS. 16A to 16D show nitrogen and methane detection curves for various carrier gases, respectively hydrogen, helium, nitrogen and argon, FIGS. 17A to 17D illustrate, with different scales in ordinates, natural gas detection curves with a reference FID detector (lower curve) and with an NEMS detector upper curve), FIGS. 18 and 19 show a read-out circuit wherein the NEMS detector comprises a heating system according to a first and a second embodiment, respectively;

FIG. 20 shows different embodiments of a NEMS detector compatible with a heating system.

DETAILED DESCRIPTION OF EMBODIMENTS OF THE INVENTION

FIG. 1 schematically illustrates the principle of a gas analysis system applying separation by gas chromatography followed by detection with at least one detector of the NEMS type.

The gas G to be analyzed is injected into a fluidic channel 3 of the analysis system 1 with an injector 2.

Downstream from the injector 2, the gas G is mixed with a carrier gas C from a source 4.

The arrow indicates the direction of the gas flow.

The carrier gas C is selected so as not to have any chemical interaction towards the gas to be analyzed.

The carrier gas C is therefore preferably a neutral gas such as hydrogen, nitrogen, helium, argon, filtered air (also called «zero air») etc.

The carrier gas then conveys the gas to be analyzed through a chromatography column 5, along which the species contained in the gas to be analyzed are separated according to their affinity towards a stationary phase laid out in the column 5.

Here, three distinct species E1, E2, E3 are illustrated, which arrive on the detector 6 laid out in the fluidic channel downstream from the chromatography column at different instants, as shown by the diagram on the lower right of the figure.

The detector typically comprises a resonator of the electromechanical nanosystem (NEMS) type, a device for actuating vibration of the resonators, and a detection device adapted so as to provide an electric output signal representative of vibrations of the resonator. As described in more detail below, the detector also comprises a heating system capable of heating at least a part of the detector and thus the surrounding gas, so as to improve the contrast between the viscosity of the carrier gas and that of the gas to be analyzed.

If necessary, said detector may be laid out in the actual inside of the chromatography column.

This embodiment is notably advantageous when these are NEMS detectors and a chromatography column formed in a silicon chip, as this is described in document WO 2011/154362.

Preferably, the system comprises a plurality of detectors laid out in one or several networks.

Within a same network, the detectors are connected in parallel, each network comprising an input and an output respectively connected to the input and to the output of each of said detectors.

Preferably, said detectors are addressed collectively, i.e. the output signal of the network is a combination of the signals of each detector.

Generally, the output signal of the network is equal to the sum of the output signals of the various detectors which make it up, and a processing system then calculates an average of this total signal.

With this arrangement, it is possible to improve the signal-to-noise ratio (SNR) and therefore to increase the performances of the network of detectors relatively to a single detector.

The networking of the detectors in particular allows compensation for the dispersions due to the manufacturing of the different resonators.

Moreover, the application of several detectors has the advantage of overcoming the deficiency of one of the detectors.

Finally, the interactions of the network of detectors with the gas are promoted, as the coupling surface area provided by the whole of the resonators is larger.

In document WO 2012/172204, a description is found of a measurement system comprising a network of detectors and of a method for reading out such a network, which may be applied in the present invention.

The detectors or networks of detectors may be laid out in different locations of the fluidic channel 3 (for example certain detectors or networks of detectors are laid out in the chromatography column and other ones downstream from the column).

On the other hand, the detectors may have different characteristics from one network to the other, so as to promote detection of several particular species.

Said various characteristics may be chemical characteristics (for example a different functionalization) or geometrical characteristics. Thus, for example, the thickness of the resonator, the length of the resonator, the width of the resonator and/or the distance between the resonator and the actuation device may be varied for modifying the properties of the detector.

In order to maximize the fluidic interactions between the detector and the gas to be analyzed, the resonator is preferably used in a flexural mode.

In known detectors, the resonator may appear as a clamped beam at one of its ends and free at the other end, or as a clamped beam at each of its ends.

The resonator is typically made by etching a semiconducting substrate (for example silicon).

In this respect reference may be made to [Mile 2010] for more details on the manufacturing of the resonator.

In a way known per se, the resonator may be vibrationally actuated by electrostatic, thermo-elastic, magnetic, piezoelectric forces.

For example, for electrostatic actuation, two actuation electrodes intended to receive an electric excitation signal and a signal with opposite sign respectively are applied on either side of the beam; said electrodes therefore form two inputs of the resonator.

In the case of a network of collectively addressed detectors, the whole of the resonators is actuated in vibration by a same excitation signal.

The detector further comprises a detection device adapted for providing an output electric signal representative of the vibrations of the resonator.

The detection device may thus comprise a capacitive sensor, a piezo-resistive strain gauge or a piezo-electric strain gauge.

In the following of the description, we consider the example of a resonator formed with clamped/free (cantilever) beam (also designated by the term of «cross-beam») with capacitive actuation and piezo-resistive detection, the description of the operating principle of which may be found in [Mile 2010] or in document EP 2 008 965.

The experimental examples shown below were actually obtained with this type of resonator.

This embodiment is however not a limitation.

Thus, according to another embodiment, the detector may comprise a metal resonator with thermo-elastic actuation and piezo-resistive detection as described in [Bargatin 2012].

FIG. 2 illustrates a resonator of the clamped/free beam type.

The beam 100 resonates in a movement in the plane of the figure and is actuated by means of two electrodes 101 located on either side of the beam.

The characteristic dimensions of this resonator are the length l of the beam 100, the width w of the beam 100, the thickness of the beam (in a plane perpendicular to that of the figure), and the gap g, i.e. the distance between the beam 100 and the actuation electrode 101.

Two piezo-resistive gauges 102 allow differential detection of the displacement of the beam 100 have a length d, a width s and a thickness identical with that of the beam.

Said gauges 102 are preferably located in the vicinity of the clamped end 100a of the beam, so as to benefit from a lever arm effect which makes the detection more accurate.

The free end of the beam 100 is designated by the mark 100c.

According to an embodiment, the measurement of the variation of electric resistance of the piezo-resistive gauges 102 is carried out between the clamped end 100a of the beam and the junction between the beam 100 and the strain gauges.

The output signal of the resonator is thus provided to a connection electrode (not shown here) located at the clamped end 100a of the beam, with view to the reading of said signal.

This measurement method is however not exclusive and the output signal may be provided by other means; for example, it is possible to apply a bias voltage at said connection electrode and to measure the voltage on the terminals of the assembly of two strain gauges 102 for inferring therefrom the change in their electric resistance.

When several detectors are connected in parallel in order to form a network and addressed collectively, the output signal of the network is a combination (for example an average) of the output signals of each resonator.

The dynamics of such a resonator may be described by means of the following simplified differential equation:

$$m\ddot{x}+b\dot{x}+kx=f_a(t)+f_f(t) \qquad (1)$$

wherein m, b, k are respectively the effective mass of the resonator, the damping due to mechanical losses in the structure, the effective stiffness of the resonator and wherein $f_a(t)$, $x(t)$ and $f_f(t)$ are respectively the electrostatic force for actuating the beam, the displacement of the beam and the fluidic interaction forces of the ambient medium with the beam $f_f(t)$.

The angular frequency specific to the resonator is equal to:

$$\omega_0 = \sqrt{\frac{k}{m}}$$

It may be shown that the electrostatic actuation force is equal to $$fa(t) = \frac{\varepsilon_0 S V(t)^2}{(g-x(t))^2} \qquad (2)$$

wherein $V(t)$ is the potential difference between the actuation electrode and the beam, $\varepsilon_0$ is the permittivity of the medium, g is the gap between the actuation electrode, S is the cross-section of the actuation electrodes.

By superposing a direct current (DC) voltage to an alternating current (AC) voltage on $V(t)$ and assuming that $x(t) \ll g(t)$, a Taylor expansion allows linearization of equation (1):

$$m\ddot{x}+b\dot{x}+(k-k_{elec})x=KV_{AC}(t)+f_f(t) \qquad (3)$$

wherein $k_{elec}$ is the negative electrostatic stiffness (dependent on the biasing conditions and on the geometry of the resonator) and K is the actuation gain (function of the geometrical parameters of the beam and of its actuation electrodes):

$$k_{elec} = \frac{2\varepsilon_0 S V_{DC}^2}{g^3}$$

Taking into account equation (2), the specific angular frequency of the resonator is modified according to:

$$\omega_0 = \sqrt{\frac{k - kelec}{m}}$$

The damping due to viscous friction stems from the interaction of the ambient gas with the mechanical structure: it is conditioned in the term $f_f(t)$.

The determination of this force resorts to the resolution of the Navier-Stokes equation for a gas:

$$\rho\left[\frac{\partial \vec{v}}{\partial t} + (\vec{v} \cdot grad)\vec{v}\right] = -grad\, p + \mu \Delta \vec{v} \quad (4)$$

wherein $\rho$ is the density of the gas, $\vec{v}$ is the velocity of the gas relatively to the resonator, p is the pressure of the gas, $\mu$ is the viscosity of the gas.

Thus, depending on the species surrounding the resonator, the expression $f_f(t)$ is modified in particular by the gas density (related to its molar mass) and its viscosity.

This equation is associated with the boundary conditions of the domain.

Within the scope of small gaps, i.e. of the order of or less than the mean free travel of the molecule of the relevant species, it is possible to simplify the Navier-Stokes equation under the so-called Reynolds equation describing the fluidic interaction forces under the term of «squeeze film damping».

This damping phenomenon predominates in NEMS with electrostatic actuation.

As regards the modeling of the squeeze film damping by means of a compact model, reference may be made to [Bao 2007].

It is possible to show that the fluidic forces exert on the resonator a force equal to:

$$f_f(t) = -c_d \dot{x} - k_e x \quad (5)$$

with $$c_d \approx \frac{64 \cdot P \cdot l \cdot e}{\pi^6 g} \cdot \sigma \text{ and } k_e \approx \frac{64 \cdot P \cdot l \cdot e}{\pi^8 g} \cdot \sigma^2 \quad (6)$$

wherein $$\sigma = \mu_{eff} \frac{12 \omega_0 e^2}{P g^2}$$

is the «squeeze» term, depending on the effective viscosity of the gas $$\mu_{eff} = \frac{\mu}{1 + 7\frac{\lambda}{g}}$$

which takes into account the gas rarefaction conditions through the mean free travel $\lambda$ of a given gas molecule (proportional to the size of the gas molecule).

It should be noted that in the literature there exist various definitions of the effective viscosity of the gas, illustrated by equations 5.5 and 5.6 in [Bao 2007].

Indeed, the effective viscosity is approximated over a given gap range, this approximation being more or less accurate depending on the width of said range.

However, regardless of the retained definition, it has no incidence on the actual principle of the measurement $\mu$ is the dynamic viscosity of the gas, l is the length of the beam, e its thickness, g the gap, $\omega_0$ the resonance frequency of the NEMS ($\omega_0$ is proportional to $$\frac{w}{l^2}$$

in the case of a clamped/free beam with w the width of the beam) and P is the pressure of the gas surrounding the NEMS.

The whole of these equations is valid in the case when the ratio $l/e \gg 1$ and $\sigma < 10$. In the opposite case, a corrective term depending on the geometrical parameters of the resonator which may be found in equations 3.7 and 3.18 of [Bao 2007] should be applied.

The mean free path of a gas molecule is described according to the following equation:

$$\lambda = \frac{k_B T}{\sqrt{2}\, \pi d_g P} \quad (7)$$

wherein $k_B$, T, $d_g$, P are respectively Boltzmann's constant, the temperature of the gas, the diameter of the gas molecule and P the pressure of the gas.

From equations (5) and (6), it is noted that for maximizing the fluidic influences (i.e. the influence of $\mu_{eff}$), it is mainly appropriate to:

reduce the gaps (as a power of 3) and/or,
increase the silicon thickness (as a power of 3).

It may also be useful to have an influence on the less predominating terms such as the pressure and temperature.

Moreover, by having an influence on the size of the gaps g, it is possible to only involve in $\mu_{eff}$ the influence of the dynamic viscosity $\mu$ (case when $\lambda \ll g$) or else the ratio $\mu/\lambda$ (case when $\lambda > g$ i.e. under gas rarefaction conditions).

Thus, by acting on the design of the NEMS resonators, it becomes possible to measure several physical parameters of the gas to be analyzed, i.e. its dynamic viscosity and its mean free path.

When dealing with NEMS resonators, the latter requires small gaps in order to exert significant actuation forces (cf. equation 2).

For these resonators, rarefaction conditions are obtained which ensures that the coefficient $c_d$ is smaller (correction of the term $\mu_{eff}$).

These nanostructures therefore give the possibility of obtaining an improved quality factor at ambient pressure of the order of 100 to 500 (a quality factor 10 times greater typically than that of a MEMS in the absence of vacuum).

Table 1 below shows a few characteristic quantities for different gases and for a typical geometry of a NEMS resonator:

| | |
|---|---|
| l (length of the beam) | [1-10] μm |
| e (thickness of the beam) | [0.01-1] μm |
| w (width of the beam) | [0.01-1] μm |
| g (gap) | [10-200] nm |
| Resonance frequency $\omega_0/(2\pi)$ | [10-100] MHz |
| Mean free path of a gas molecule λ | [40-200] nm at atmospheric pressure (100 kPa) |
| Pressure P | 100 kPa |
| Dynamic viscosity | [80-250] μPoises |
| Squeeze term σ | <5 |

Table 2 below provides the viscosity and the mean free path for a few gases:

| | Dynamic viscosity (μPoise) | Mean free path at ambient pressure (nm) | Effective viscosity with a gap of 150 nm (μPoise) | Dynamic viscosity normalized relatively to $N_2$ | Effective viscosity normalized relatively to $N_2$ |
|---|---|---|---|---|---|
| Hydrogen | 86.50 | 110.00 | 14.10 | 0.52 | 0.31 |
| Helium | 186.30 | 173.00 | 20.53 | 1.12 | 0.46 |
| Methane | 102.70 | 48.00 | 31.70 | 0.62 | 0.71 |
| Neon | 297.40 | 124.00 | 43.82 | 1.79 | 0.99 |
| Nitrogen | 165.70 | 58.80 | 44.26 | 1.00 | 1.00 |
| Air | 179.00 | 60.00 | 47.11 | 1.08 | 1.06 |
| Oxygen | 190.90 | 63.00 | 48.45 | 1.15 | 1.09 |
| CO2 | 137.20 | 39.00 | 48.65 | 0.82 | 1.10 |
| Argon | 209.90 | 62.00 | 53.91 | 1.26 | 1.22 |

According to Table 2, it is observed that by taking into account the rarefaction conditions, the effective viscosity is modified.

Thus, it is observed for gaps of 150 nm as an example, that hydrogen is less viscous than helium, which itself is less viscous than methane.

Therefore, and taking into account the typical values used in the field of NEMS, it may be written that:

$$c_d \propto \frac{we^3}{lg^3}\mu_{\textit{eff}} \text{ and } k_e \propto \frac{1}{P}\frac{w^2e^5}{l^3g^5}\mu_{\textit{eff}}^2 \quad (8)$$

Equation (3) may then be rewritten as follows:

$$m\ddot{x}+(b+c_d)\dot{x}+(k-k\text{elec}+k_e)x=KV_{AC}(t)$$

Thus, the resonance frequency of the NEMS resonator is modified in the following way:

$$\omega_f \sqrt{\frac{k-k_{elec}+k_e}{m}} = \omega_0\left(1 + \frac{k_e}{2(k-k_{elec})}\right) \quad (9)$$

The quality factor of the NEMS resonator is also modified as follows:

$$Q = \frac{\sqrt{(k-k_{elec}+k_e)m}}{b+c_d} \approx \frac{\sqrt{km}}{c_d} \quad (10)$$

In equation (10), it is assumed that fluidic losses are greater than mechanical losses (b«$c_d$).

Moreover, the influence of $k_e$ is negligible in the expression of the quality factor taking into account the characteristic dimensions of the NEMS resonators ($k_e$«k).

At resonance $\omega_f$, the gain G in amplitude of the resonator is then proportional to:

$$G \propto \frac{1}{c_d} \quad (11)$$

Thus, with the real time measurement of the resonance frequency $\omega_f$ of the resonator and of the amplitude at resonance, it is possible to obtain the fluidic properties of the gas $\mu_{\textit{eff}}$ and $\mu_{\textit{eff}}^2$.

Upon passing of the species of interest in the vicinity of the NEMS resonator, the variation of the amplitude of the vibrations relatively to the carrier gas is then equal to:

$$\Delta G = G1 - G2 \propto \frac{C_{d1} - C_{d2}}{C_{d1} \cdot C_{d2}} \propto \frac{lg^3}{we^3}\frac{\Delta\mu_{\textit{eff}}}{\mu_{\textit{eff}1} \cdot \mu_{\textit{eff}2}}$$

wherein $G_1$ and $G_2$ are the vibrational gains under a given carrier gas and under the species of interest, $c_{d1}$ and $c_{d2}$ are the fluidic losses associated with the carrier gas and with the species of interest.

In order to maximize the detection of a gas species conveyed in the chromatographic separation column by a given carrier gas, it is preferable to maximize the contrast (i.e. the ratio) of the effective viscosities and/or to reduce the thickness e of the resonators as well as their width w.

In other words, passing to the resonator at a nanometric scale (NEMS) is particularly favorable to detection accuracy.

On the other hand, it is preferable to use large gaps (but not exceeding the value of the mean free pass of the molecules in order to remain under the gas rarefaction conditions, while making sure not to increase them too much in order to ensure proper actuation of the resonator (cf. equation 2) with biased voltages of the order of one volt.

Thus, gaps comprised between 50 nm and 250 nm are typically used.

According to Table 2, the gases which may be contemplated as carrier gases are, hydrogen, helium and argon (non-exhaustive list).

However, according to the needs of the application (notably in terms of measurement resolution and/or detection limit terms) other types of carrier gases may be contemplated, for example air or nitrogen for detecting methane.

From an electronic point of view, simultaneous measurement of the resonance frequency of the resonator as well as the amplitude of the vibrations at the resonance frequency is conducted by loading the detector in a phase locked loop (PLL) or in an oscillator.

FIG. 3 is a block diagram of the electronic read-out circuit comprising a phase locked loop.

In the PLL type measurement of a resonator, the variation of the resonance frequency of the resonator is followed continuously over time.

Said read-out circuit is advantageously designed for jamming a frequency of the excitation signal on the frequency of a resonance peak of the output signal of the network and for providing, as an excitation resonance frequency, the jammed frequency.

For this purpose, the PLL circuit comprises a voltage-controlled oscillator VCO which is controlled by a voltage F and connected to an input of a detector or of a network of detectors noted as NEMS, for providing it with a periodic and single frequency excitation signal with a frequency corresponding to the frequency of the voltage F.

The LNA component is a low noise amplifier.

This read-out scheme applies synchronous (lock-in) detection which gives the possibility of measuring simultaneously:

after comparison with the phase comparator means COMP, the phase shift induced between the excitation signal of the resonator (phase φrd) and its measured signal (phase φ), and the vibrational amplitude A of the oscillations.

In order to be subordinated to the resonance frequency F of the resonator, the frequency of the excitation oscillator of the VCO (Voltage Control Oscillator) resonator is adjusted so as to maintain a constant phase shift by means of a corrector CORR (PI type) connected to the comparator COMP.

FIG. 4 is a block diagram of the electronic read-out circuit comprising an oscillator.

In the measurement of the oscillator type, a reaction filter is associated with the resonator so as to cause self-oscillation of the resonator on its resonance frequency.

The measurement of the amplitude of the oscillations is conducted by means of automatic gain control (AGC), the role of which is to adjust the gain (AG) of the reaction loop so as to maintain the amplitude A of the oscillations constant.

The PS (phase shifter) component gives the possibility of ensuring the proper phase shift between the output and the input of the detector in order to permanently sustain the oscillations.

The gain of the reaction filter then represents in this architecture an «image» of the amplitude of the oscillations.

The frequency F of the oscillations is measured by means of a frequency counter FC.

It is obvious that the electronic read-out circuit may be designed according to a different scheme from the principles illustrated in FIGS. 3 and 4 without however departing from the scope of the invention if it gives the possibility of simultaneously providing the amplitude and the vibrational frequency of the resonator.

In addition to the measurement of the fluidic parameters of the species of interest, it is possible to also conduct with the same detector or network of detectors a gravimetric measurement as described in [Arcamone 2011].

The principle of the gravimetric measurement is based on the chemical interaction of a functionalization layer with the species to be measured.

The gas species is actually adsorbed and desorbed successively at the surface of the resonator, causing a modification of the effective mass of the resonator and reducing the resonance frequency of the resonator (cf. equation 9).

Different chemical functionalization layers (notably polymers, inorganic layers such as porous SiOC, porous Si), may be used for promoting these adsorption/desorption phenomena.

The gravimetric measurement is particularly more sensitive than the measurement by fluidic interaction for low gas concentrations.

On the other hand, it requires having functionalization layers having good chemical affinities with the gases to be detected.

In this sense, the gravimetric approach is less universal than the approach by fluidic interaction measurements but is well applied for not very volatile species.

The approach by measurement of fluidic interaction is particularly applied to highly volatile compounds such as rare gases, methane, ethane, carbon dioxide, dioxygen, etc.

This approach is therefore universal and is very efficient for relatively substantial gas concentrations (i.e. greater than a few hundred ppm).

Thus, the measurement by fluidic interaction lends itself particularly well to gas chromatography, in which it is possible to control via the injection parameters the amounts of injected material (volume of sampled species) in the column and where one operates under a controlled atmosphere by means of the carrier gas.

On the other hand, the fluidic interaction with a porous layer deposited at the surface of the resonator may advantageously be used for measuring the viscosity of the gas.

By «porous» is meant here a microporous or coarsely nanoporous layer, i.e. for which the size of the pores is comprised between a few nanometers and a few hundred nanometers.

The material of this porous layer may be porous SiOC or Si.

As seen above, the resonance measurement based on NEMS resonators gives the possibility of accessing the different degrees of separation, i.e. the variation of the mass of the resonator by the adsorption/desorption phenomena, and the variation of the stiffness of the resonator and fluidic losses by interaction with the surrounding gas according to equation 8.

Each of the physical phenomena set into play aims at a range and at a given specificity of the gas to be measured.

Gravimetric measurement is thus preferred for heavy compounds in low concentration ranges (ppm to sub-ppm) and measurement by fluidic interaction for highly volatile light compounds in relatively large concentration ranges (from a few hundred ppm to 100%).

It is moreover possible to simultaneously measure the first resonance modes of the resonator.

Now, the more the relevant frequency of the mode increases and the more the quality factor of the resonator increases.

Therefore it is possible to simultaneously carry out a gravimetric measurement on a selected mode (typically the first resonance mode) and a fluidic coupling measurement on one or several other higher modes relatively to said selected mode.

In this respect, the application of a detector as illustrated in FIG. 9A provides good results.

Moreover, passing to a nanometric scale (NEMS resonators as compared to MEMS resonators) exacerbates the whole of these phenomena.

It is also possible to have on a same chip NEMS detectors or networks of NEMS detectors without any chemical functionalization layer (for the measurement of viscosity) and other detectors or networks of detectors with a chemical functionalization layer adapted for the gravimetric approach, which will allow simultaneous measurement according to both principles by separating them as best as possible (lack of correlation).

Because of their nanometric size, the NEMS detectors or networks of detectors may be embedded, by means of manufacturing technologies stemming from microelectronics, directly in or downstream from the fluidic channel of the chromatographic separation column for the species.

On a silicon chip comprising a fluidic channel and NEMS detectors, it is possible to integrate one or several NEMS detectors or networks of detectors, each specifically dealing with one physical characteristic of the gas to be measured.

FIGS. 5, 6 and 7 show possible exemplary embodiments of the fluidic channel.

By modulating the section of the fluidic channel, it is possible to locally modify the gas flow in the channel and therefore the pressure surrounding the NEMS resonator in order to exacerbate fluidic phenomena and thus improve detection.

This adjustment is based on the Venturi effect (Bernouilli's law).

FIG. 5 provides a schematic illustration of a fluidic channel 3 in which are loaded three detectors or networks of detectors NEMS1, NEMS2, NEMS3.

The section of the fluidic channel is preferably identical with that of the separation column (typical value: 100 µm×100 µm).

In this embodiment, the cross-section is constant in order to keep constant flow and pressure.

Nevertheless, it is possible to structure this channel in a different way in order to modify the pressure/temperature conditions in the channel by the Venturi effect and thus more or less exacerbate the interactions of each NEMS resonator with the gas surrounding it.

Thus, FIG. 6 illustrates an embodiment in which the section of the fluidic channel 3 is modulated in order to locally modify the pressure in the channel by the Venturi effect and thus promote fluidic interactions.

In this case, a section restriction 30 generates a depression area D in the shrunk portion, responsible for local acceleration of the flow, while a compression area C is generated upstream from the shrunk portion 30.

By positioning the detectors or networks of detectors NEMS1, NEMS3 and NEMS2 upstream, downstream and in the depression area D, respectively, it is possible to obtain a measurement of the fluidic interactions (cf. equation 8) under different pressure conditions.

FIG. 7 illustrates another embodiment in which the section of the fluidic channel is modulated for causing pressure variations.

In this case, widening of the section 31 generates a compression area C in the widened portion, responsible for local slowing down of the flow, while a depression area D is generated downstream from the widened portion.

By positioning the detectors or network of detectors NEMS1, NEMS3 and NEMS2 upstream, downstream, and in the depression area C respectively it is possible to obtain a measurement of the fluidic interactions (cf. equation 8) under different pressure conditions.

On the other hand, it is possible to couple the detector or network of detectors to a vacuum pump laid out downstream from said detector or network of detectors, in order to reduce the pressure of the gas surrounding the resonator and thus modify the interactions between the resonator and the surrounding gas.

FIG. 8 thus illustrates a gas analysis system comprising a chromatography column GC, a plurality of detectors or networks of detectors D laid out in a fluidic channel 3 downstream from the column and a vacuum pump P downstream from said detectors or networks of detectors D allowing decrease in the pressure in the column and thus exacerbating the interactions between the resonators and the gas.

Said vacuum pump may be advantageously used as a first stage of a mass spectrometer, in order to practice other measurements of the gas, complementary to the measurements conducted by means of the detector.

It is considered that the application of a primary vacuum of the order of $10^{-3}$ or $10^{-4}$ torrs is sufficient for providing the aforementioned advantages.

FIGS. 9A and 9B illustrate other examples of NEMS detectors which may be applied in the invention.

The elements fulfilling the same function as those of the detector illustrated in FIG. 2 are designated with the same reference symbol.

In both cases, the resonator is a beam 100 which is clamped at its two ends 100a, 100b.

In this respect reference may be made to document WO 2012/034990, which describes such detectors.

Unlike a clamped/free beam, a clamped/clamped beam has resonance modes from the second mode which are closer in frequency than the main mode 1.

Thus, it is easier with this type of resonator of aiming at the higher modes which by their nature have better quality factors.

FIG. 10 illustrates another example of a NEMS detector, wherein the resonator is a beam 100 free at its two ends 100a, 100b and which is held in its central portion by two gauges 102 also intended for detection.

Document WO 2012/034951 describes such a detector type.

Moreover, an increase in the temperature of the gas has the effect of improving the contrast between the viscosity of the carrier gas and that of the gas to be detected.

By heating the chromatography column and by maintaining it at a constant temperature (for example up to 100° C. or 150° C.) and by placing the detector or network of detectors just at its output (in order to minimize any heat loss of the gas between the column and the detector), it is thus possible to improve the detection performances during the amplitude measurement of the resonator.

The application of a stronger bias voltage on the piezo-resistive gauges of the NEMS resonators or of the resonators themselves also allows potentially intense local heating of the gauges or of the NEMS resonator by the Joule effect (up to 500° C. for example) and therefore of the gas circulating right around it.

This allows an increase in the viscosity contrast via the amplitude measurement.

Moreover by heating the detector or network of detectors, this effect degrades or even suppresses the adsorption mechanisms (physisorption and chemisorption) on the NEMS resonator and therefore minimizes the gravimetric detection principle to the benefit of the viscosity measurement.

To that end, each detector comprises a heating system that is configured to heat at least a part of the detector. Preferably, this heating system is an electrical heating system and the heat is generated by Joule effect.

According to an embodiment, the heating system comprises a DC voltage source 103 coupled to the piezo-resistive gauges 102 to apply a DC voltage on them, as shown in FIG. 18, which illustrates a read-out circuit wherein the NEMS detector comprises a resonator 100 of the clamped/free beam type (also illustrated in FIG. 2 and in FIG. 20 (referred to as X beam)). For example, the resistance of the piezo-resistive gauges 102 is in the kOhm range with doped silicon of 5 à $7.5 \times 10^{19}$ $cm^{-3}$ and the gauge dimensions are of 1 µm in length, 160 nm in thickness and 80 nm in width. According to these values, by applying a DC voltage of a few volts (typically 5V), one can raise the temperature of the detector of a few hundred ° C. (typically 200° C.) above room temperature.

Although the piezo-resistive gauges can be directly used to self-heat the detector, there are some limitations because these gauges can withstand a limited electrical current due to their relatively small cross-section (80 nm×160 nm); in other words, the gauges may behave as a fuse if a too large electrical current is applied. To overcome this issue, another embodiment, shown in FIG. 19, uses a clamped-clamped beam structure 100 instead of a clamped-free beam. In this case, the heating system comprises a DC voltage source 103 coupled to the beam 100 itself, so that an electrical current passes through the beam and it's the beam by Joule effect.

This self-heating system can be applied equivalently to the T beam, H beam and HBT beam devices as shown in FIG. 20. The HBT beam has U shape actuation electrode 101 so that the gap g between the beam 100 and the electrode 101 is maximized in order to increase fluidic interactions between the beam and the surrounding gas. All these devices are etched on a doped silicon on insulator wafer.

With at least two detectors or networks of detectors comprising identical NEMS resonators and the application of a stronger bias voltage on the piezo-resistive gauges or on the resonators of a single one of the detectors or networks of detectors, it is thus possible to simultaneously conduct a gravimetric measurement (frequency measurement) and a measurement of viscosity (amplitude measurement) by decorrelating as best as possible both mechanisms.

In a gas chromatograph (GC) instrument, the above devices can be used to measure peaks of gases coming out of the GC column. The column is used to separate and identify (identification is achieved with the retention time) the different gases composing the mixture that is analyzed.

In order to detect the different peaks of gases, one can use the viscosity contrast between the compounds and the carrier gas as discussed previously. To measure the viscosity changes, one can track the vibration amplitude of the NEMS at its resonance frequency. As explained above, to improve the limit of detection, i.e. the contrast between the carrier gas and the compounds to measure, the temperature of the NEMS detector should be as high as possible.

By coating the NEMS resonator with a specific functionalization layer (e.g. a porous oxide deposit on top the NEMS resonator) capable of chemically interacting with the gas to be analyzed, another detection principle based on adsorption/desorption principle can be used. While the gas is adsorbed by the NEMS resonator, it modifies its effective mass and as a consequence its resonance frequency. Therefore to monitor the quantity of gas adsorbed, one can track the NEMS resonance frequency with the same electronic device as used to measure viscosity changes. To improve the limit of detection i.e. the quantity of gas adsorbed at the NEMS surface, the temperature of the NEMS should stay as low as possible (but above the gas boiling point).

Therefore, using a unique NEMS detector or networks of detectors polarized with different electrical conditions to heat or not the NEMS detector, one can detect different physical properties of the gas:
- when the NEMS detector is at a high temperature, viscosity contrast is measured;
- when the NEMS is at a low temperature, adsorption/desorption between the functionalization layer and the gas is measured.

Finally, as regards the processing of the signal, it is possible to benefit from the multidimensional nature of the detector or network of NEMS detectors in order to implement data merging algorithms.

An example of data merging consists of linearly summing the amplitude measurement and the frequency measurement according to the following equation:

$$\text{output}(t) = \frac{f(t) + K \cdot M(t)}{1 + K}$$

wherein output is the resulting signal from the merging, f(t) is the resonance frequency measurement, M(t) is the amplitude measurement, K is an adjustable gain.

For example, if $\|K\| \gg 1$ is selected, the amplitude signal will be preferred to the detriment of the frequency signal.

If $\|K\| \ll 1$ is selected, the frequency signal will on the contrary be preferred to the detriment of the amplitude signal.

Typically K=1 is selected for assigning equal importance to the frequency signal and to the amplitude signal.

Experimental Results

The series of results which follows is an illustration of the fluidic detection possibilities provided by the NEMS resonators.

As an example, methane (noted as C1), ethane (noted as C2) and natural gas were tested with different carrier gases.

Depending on the type of carrier gas used, the amplitude of the oscillations at the resonance of the NEMS resonator may vary positively or negatively upon passing of the species of interest to be measured.

In order to determine the variation direction of the amplitude peaks, reference may be made to Table 2 which provides the effective viscosity (homogeneous to the physical quantity) for different gases of interest.

Thus, when the intention is to measure methane (C1) under a carrier gas of the argon, nitrogen or air type, positive peaks are obtained on the amplitude because of a lower effective viscosity for these gases and for methane.

Moreover, a larger amplitude response is obtained under argon since it is for this carrier gas that the effective viscosity contrast with C1 is the most significant.

In the case when helium or hydrogen is used as a carrier gas, negative peaks on the amplitude are obtained with larger peaks in the case of hydrogen, the contrast of the effective viscosities being higher.

The experiments were carried out on a piece of gas chromatography GC equipment equipped with an injection port IP, with an oven O and with a FID detector, used as a reference detector.

As illustrated in FIG. 11, a detector comprising a NEMS resonator placed at room temperature is connected downstream from the chromatography column GC and upstream from the FID detector through a deactivated capillary c.

1—Separation and Detection of Nitrogen and Methane Under Hydrogen

FIGS. 12A to 12C illustrate the chromatograms (response expressed in an arbitrary unit) obtained during injection of 100 μL of an equal-volume mixture of methane and air (FIG. 12B) and of pure methane (FIG. 12A). FIG. 12C shows the superposition of both of these curves.

The separation is achieved with hydrogen as a carrier gas at 10 psi (68.95 kPa) on a commercial column Restek MTX-Q-Bond of (7 m×0.25 mm×8 μm) at 60° C.

The column separates methane from the other non-retained compounds such as nitrogen ($N_2$) into two peaks which are detectable with the NEMS detector.

2—Linearity of the Response of the NEMS Detector to Methane and Ethane Under Hydrogen Different amounts of C1 and C2 are injected and separated under the conditions described in paragraph 1.

FIG. 13 illustrates the detection curve (response expressed in arbitrary units) with the NEMS detector for two different injected amounts of methane.

The areas (expressed in arbitrary units) of the peaks obtained with the NEMS detector (right ordinate axis—squares) and the FID detector (left ordinate axis—disks) are reported according to the injected volumes, for methane (FIG. 14A) and for ethane (FIG. 14B), respectively.

The response of both detectors is linear over the whole tested range.

3—Separation and Detection of Nitrogen and Methane Under Different Carrier Gases The response of the NEMS detector to injection of methane was studied for various carrier gases.

FIG. 15 illustrates the chromatograms (response expressed in arbitrary units) obtained during the separation of methane from the non-retained compound under hydrogen, helium, nitrogen and argon.

It is observed that the quality factor (which is linearly inversely proportional to the fluidic losses) is improved when passing from argon to nitrogen, from nitrogen to helium and from helium to hydrogen.

With nitrogen or argon as a carrier gas, there is an improvement in the quality factor upon passing of methane, which causes an increase in the vibrational amplitude.

On the contrary, with helium or hydrogen as a carrier gas, the quality factor is degraded upon passing of methane, which causes a negative change in the vibrational amplitude.

FIG. 16 illustrates a separation and a detection of nitrogen and methane under different carrier gases (response expressed in arbitrary units). The separation is carried out under the conditions described in paragraph 1.

The illustrated curves correspond to the crude signals (without any processing).

4—Analysis of Natural Gas: Separation and Detection

In another experiment, natural gas was injected under the conditions described above with hydrogen as a carrier gas.

The column allows separation of $CO_2$, methane and ethane from the non-retained compounds.

As this may be seen in FIGS. 17A and 17B, which has different scales, all these compounds are detected by the NEMS resonator (upper curve), the methane (C1) and the ethane (C2) being characterized by their retention time which is determined with the FID detector (lower curve).

REFERENCES

[Arcamome 2011] J. Arcamone, A. Niel, V. Gouttenoire, M. Petitjean, N. David, R. Barattin, M. Matheron, F. Ricoul, T. Bordy, H. Blanc, J. Ruellan, D. Mercier, N. Pereira-Rodrigues, G. Costa, V. Agache, S. Hentz, J C Gabriel, F. Baleras, C. Marcoux, T. Ernst, L. Duraffourg, E. Colinet, E. B. Myers, M. L. Roukes, P. Andreucci, E. Oilier, P. Puget, «VLSI silicon multi-gas analyzer coupling gas chromatography and NEMS detectors», IEDM11, pp. 669-672

[Mile 2010] E. Mile, G. Jourdan, I. Bargatin, S. Labarthe, C. Marcoux, P. Andreucci, S. Hentz, C. Kharrat, E. Colinet, L. Duraffourg, In-plane nanoelectromechanical resonators based on silicon nanowire piezoresistive detection, Nanotechnology 21, (2010) 165504

[Bargatin 2012] I. Bargatin, E. B. Myers, J. S. Aldridge, C. Marcoux, P. Brianceau, L. Duraffourg, E. Colinet, S. Hentz, P. Andreucci, M. L. Roukes, Large-Scale Integration of Nanoelectromechanical Systems for Gas Sensing Applications, NanoLetters 12, 1269-1274 (2012)

[Bao 2007] M. Bao, H. Yang, Squeeze film air damping in MEMS, Sensors and Actuators A 136 (2007) 3-27

[Fanget 2011] Fanget, S., Hentz, S., Puget, P., Arcamone, J., Matheron, M., Colinet, E., Andreucci, P., et al. (2011). Gas sensors based on gravimetric detection—A review. Sensors and Actuators B: Chemical, 160(1), 804-821. doi:10.1016/j.snb.2011.08.066

[Xu 2006] Y. Xu, J-T Lin, B. W. Alphenaar, R. S. Keynton, Viscous Damping of microresonators for gas composition analysis, Appl. Phys. Lett. 88, 143513 (2006)

WO 2011/154362

EP 2 008 965

WO 2012/034990

WO 2012/034951

WO 2012/172204

The invention claimed is:

1. A gas analysis system comprising:
   a fluidic channel intended for the flow of a gas to be analyzed,
   at least one detector laid out in said fluidic channel and adapted for measuring interactions of the gas with said detector, said detector comprising at least one resonator of the electromechanical nanosystem (NEMS) type,
   an actuation device for vibrationally actuating the resonator according to an excitation signal applied to an input of the detector, and
   a detection device adapted for providing an output electric signal representative of the vibrations of said resonator,
   a read-out device connected to an input of the detector and configured for simultaneously measuring, from the output signal of said at least one detector, the change in resonance frequency and the change in amplitude of the vibrations at the resonance frequency of the resonator, and
   a processing device configured for determining from said changes at least one of a viscosity and an effective viscosity of said gas,
   wherein the at least one detector comprises an electrical heating system operable for heating at least a part of the resonator or the detection device by Joule effect.

2. The system of claim 1, comprising a plurality of detectors electrically connected in parallel so as to form at least one network having:
   at least one input for applying, with the read-out device, at least one excitation signal in vibration, to the whole of the detectors of the network, and
   at least one output for providing a signal resulting from the output signals of each of the detectors of the network.

3. The system of claim 2, wherein said resulting signal includes the different output signals of the detectors connected in parallel and the processing device is configured for calculating an average of the output signal of the detectors of the network.

4. The system of claim 2, wherein said fluidic channel locally has a restriction and/or a widening of its cross-section and the system comprises detectors or networks of detectors laid out in portions of the fluidic channel having different cross-sections.

5. The system of claim 1, further comprising a chromatography column, the fluidic channel being laid out in at least a downstream portion of the chromatography column relatively to the direction of flow of the gas and at least a portion of said detectors or network of detectors being in said column.

6. The system of claim 1, comprising at least two detectors or networks of detectors, the resonators of which are functionalized with different chemical species.

7. The system of claim 1, wherein at least two detectors of a same network of two detectors of networks of distinct detectors have at least one different geometrical characteristic.

8. The system of claim 7, wherein said at least one different geometrical characteristic of a detector is selected from: the thickness of at least one resonator, the length of at least one resonator, the width of at least one resonator, the distance between at least one resonator and the actuation device.

9. The system of claim 1, further comprising a vacuum pump downstream from said fluidic channel.

10. The system of claim 1, wherein said processing device is further configured for applying an algorithm with which the frequency and amplitude variation measurements may be merged.

11. The system of claim 1, wherein the read-out device comprises a phase locked loop (PLL).

12. The system of claim 1, wherein the read-out device comprises an oscillator.

13. The system of claim 1, wherein the read-out device is configured, for a selected resonance mode of the detector, for measuring the resonance frequency on said selected resonance mode of the detector and optionally for measuring the amplitude of the vibrations on at least one higher resonance mode than said selected mode.

14. The system of claim 1, wherein the resonator is a beam clamped at one of its ends and free at the opposite end and wherein the detection device comprises two piezo-resistive strain gauges laid out on either side of said beam in the vicinity of the clamped end, the heating system being configured to heat the strain gauges by Joule effect.

15. The system of claim 1, wherein the resonator is a beam clamped at both ends, the heating system being configured to heat the beam by Joule effect.

16. The system of claim 1, comprising at least one detector or network of detectors, each resonator of which is functionalized with a porous layer.

17. A method for analyzing a gas, wherein:
a gas to be analyzed is injected into a gas analysis system comprising:
a fluidic channel intended for the flow of a gas to be analyzed, wherein the gas is carried by a carrier gas,
at least one detector laid out in said fluidic channel and adapted for measuring interactions of the gas with said detector, said detector comprising at least one resonator of the electromechanical nanosystem (NEMS) type,
an actuation device for vibrationally actuating the resonator according to an excitation signal applied to an input of the detector, and
a detection device adapted for providing an output electric signal representative of the vibrations of said resonator,
an electrical heating system operable for heating at least a part of the resonator or the detection device by Joule effect,
a read-out device connected to an input of the detector and configured for simultaneously measuring, from the output signal of said at least one detector, the change in resonance frequency and the change in amplitude of the vibrations at the resonance frequency of the resonator, and
a processing device configured for determining from said changes at least one of a viscosity and an effective viscosity of said gas,
the heating system is operated to increase a viscosity contrast between the gas to be analyzed and the carrier gas in a vicinity of the heated part of the resonator or detection device,
at least one resonator of a detector or network of detectors of said system is actuated for causing vibration of said resonator at a resonance frequency,
an output signal representative of the vibration of the resonator or of the whole of the resonators of said detector or network of detectors is read out, and
the resonance frequency and the amplitude of the vibrations at the resonance frequency of each detector are measured from the output signal simultaneously, and
a viscosity and an effective viscosity of the gas is determined from changes in said resonance frequency and amplitude.

18. The method of claim 17, wherein a depression is formed in the fluidic channel in which is laid out said at least one detector or network of detectors.

19. The method of claim 17, wherein the gas to be analyzed is injected into the system with a carrier gas and wherein said carrier gas is selected so that it has at least one fluidic characteristic different from that of the gas to be analyzed.

20. The method of claim 19, wherein the gas is heated upstream from the detector or from the network of detectors and/or said detector or network of detectors is heated so as to increase the contrast between said different fluidic characteristic of the carrier gas and that of the gas to be analyzed.

21. The method of claim 17, wherein a merging algorithm is applied with which the frequency and amplitude variation measurements may be merged.

22. A method for analyzing a gas, wherein:
a gas to be analyzed is injected into a gas analysis system comprising:
a fluidic channel intended for the flow of a gas to be analyzed,
at least one detector laid out in said fluidic channel and adapted for measuring interactions of the gas with said detector, said detector comprising at least one resonator of the electromechanical nanosystem (NEMS) type,
an actuation device for vibrationally actuating the resonator according to an excitation signal applied to an input of the detector, and
a detection device adapted for providing an output electric signal representative of the vibrations of said resonator,
a read-out device connected to an input of the detector and configured for simultaneously measuring, from the output signal of said at least one detector, the change in resonance frequency and the change in amplitude of the vibrations at the resonance frequency of the resonator, and
a processing device configured for determining from said changes at least one fluidic characteristic of said gas,
at least one resonator of a detector or network of detectors of said system is actuated for causing vibration of said resonator at a resonance frequency,
an output signal representative of the vibration of the resonator or of the whole of the resonators of said detector or network of detectors is read out, and
the resonance frequency and the amplitude of the vibrations at the resonance frequency of each detector are measured from the output signal simultaneously, wherein the resonance frequency is measured on a selected resonance mode of the detector and the amplitude of the vibrations is measured on at least one higher resonance mode than said selected mode.

23. A gas analysis system comprising:
a fluidic channel intended for the flow of a gas to be analyzed,
at least one detector laid out in said fluidic channel and adapted for measuring interactions of the gas with said detector, said detector comprising at least one resonator of the electromechanical nanosystem (NEMS) type and a heating system for heating at least a part of the detector,
an actuation device for vibrationally actuating the resonator according to an excitation signal applied to an input of the detector, and
a detection device adapted for providing an output electric signal representative of the vibrations of said resonator,
a read-out device connected to an input of the detector and configured for simultaneously measuring, from the output signal of said at least one detector, the change in resonance frequency and the change in amplitude of the vibrations at the resonance frequency of the resonator, and
a processing device configured for determining from said changes at least one of a viscosity and an effective viscosity of said gas,
wherein the resonator is a beam clamped at one of its ends and free at the opposite end and wherein the detection device comprises two piezo-resistive strain gauges laid out on either side of said beam in the vicinity of the clamped end, the heating system being configured to heat the strain gauges by Joule effect.

24. A gas analysis system comprising:
a fluidic channel intended for the flow of a gas to be analyzed,
a plurality of detectors laid out in said fluidic channel and adapted for measuring interactions of the gas with said detector, each detector comprising at least one resonator of the electromechanical nanosystem (NEMS) type and a heating system for heating at least a part of the detector,
an actuation device for vibrationally actuating the resonator according to an excitation signal applied to an input of the detector, and
a detection device adapted for providing an output electric signal representative of the vibrations of said resonator,
a read-out device connected to an input of the detector and configured for simultaneously measuring, from the output signal of said at least one detector, the change in resonance frequency and the change in amplitude of the vibrations at the resonance frequency of the resonator, and
a processing device configured for determining from said changes at least one of a viscosity and an effective viscosity of said gas,
wherein the plurality of detectors are electrically connected in parallel so as to form at least one network having:
at least one input for applying, with the read-out device, at least one excitation signal in vibration, to the whole of the detectors of the network, and
at least one output for providing a signal resulting from the output signals of each of the detectors of the network,
wherein said resulting signal includes the different output signals of the detectors connected in parallel and the processing device is configured for calculating an average of the output signal of the detectors of the network.

* * * * *